(12) United States Patent
Cholette

(10) Patent No.: US 9,180,293 B2
(45) Date of Patent: Nov. 10, 2015

(54) DETECTION OF FEEDING INTENT FOR USE IN TREATMENT OF EATING DISORDERS

(71) Applicant: PACESETTER, INC., Sylmar, CA (US)

(72) Inventor: Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 182 days.

(21) Appl. No.: 13/931,543

(22) Filed: Jun. 28, 2013

(65) Prior Publication Data

US 2013/0345772 A1 Dec. 26, 2013

Related U.S. Application Data

(63) Continuation of application No. 12/196,985, filed on Aug. 22, 2008, now Pat. No. 8,498,707.

(51) Int. Cl.
   *A61N 1/36* (2006.01)
   *A61B 5/0488* (2006.01)
   *A61B 5/00* (2006.01)

(52) U.S. Cl.
   CPC ........ *A61N 1/36007* (2013.01); *A61B 5/04884* (2013.01); *A61B 5/42* (2013.01); *A61B 5/4866* (2013.01); *A61N 1/36114* (2013.01); *A61B 5/416* (2013.01)

(58) Field of Classification Search
   CPC .... A61B 5/04884; A61B 5/4866; A61B 5/42; A61N 1/36114; A61N 1/36007
   See application file for complete search history.

(56) References Cited

U.S. PATENT DOCUMENTS

| | | |
|---|---|---|
| 5,263,480 A | 11/1993 | Wernicke et al. |
| 6,243,607 B1 | 6/2001 | Mintchev et al. |
| 6,449,511 B1 | 9/2002 | Mintchev et al. |
| 6,826,428 B1 | 11/2004 | Chen et al. |
| 2003/0018367 A1 | 1/2003 | DeLorenzo |
| 2004/0059393 A1 | 3/2004 | Policker et al. |
| 2004/0147816 A1 | 7/2004 | Policker et al. |
| 2005/0149141 A1 | 7/2005 | Starkebaum |
| 2005/0153885 A1 | 7/2005 | Yun et al. |
| 2005/0245986 A1 | 11/2005 | Starkebaum |
| 2006/0074450 A1 | 4/2006 | Boveja et al. |
| 2006/0161217 A1 | 7/2006 | Jaax et al. |
| 2006/0247722 A1* | 11/2006 | Maschino et al. ............. 607/40 |
| 2007/0106337 A1 | 5/2007 | Errico et al. |
| 2007/0162084 A1* | 7/2007 | Chen et al. ..................... 607/40 |
| 2008/0086179 A1 | 4/2008 | Sharma |
| 2009/0316925 A1 | 12/2009 | Eisenfeld et al. |
| 2011/0034968 A1 | 2/2011 | Knudson et al. |

OTHER PUBLICATIONS

Chen, J. et al., "Response of the electric activity in the human stomach to water and a solid meal," Med. & Biol. Eng. & Comput. 1991;29:351-367.
Di Bella, L. et al., "Behavioral Patterns Proceeding from Liver Thermoreceptors," Physiology & Behavior. 1981;26:53-59.
(Continued)

*Primary Examiner* — Catherine Voorhees

(57) ABSTRACT

An exemplary method for treating obesity includes an pulse generator configured to deliver electrical energy to a vagal nerve, one or more sensors configured to detect pre-prandial activity and, in response to the detection of pre-prandial activity, a pulse generator configured to deliver electrical energy to the stomach to induce satiety. Various other technologies are also disclosed.

11 Claims, 12 Drawing Sheets

(56) References Cited

OTHER PUBLICATIONS

Mattes, Richard D. Ph.D, RD, "Physiologic responses to sensory stimulation by food: Nutritional implications," J Am Diet Assoc. 1997;97:404-410,413.

Nederkoorn, C. et al., "Cephalic phase responses, craving and food intake in normal subjects," Appetite. 2000;35:45-55.

Nederkoorn, Chantal et al., "Cue reactivity and regulation of food intake," Eating Behaviors. 2002;3:61-72.

Nederkoorn, Chantal et al., "Exposure to binge food in bulimia nervosa: finger pulse amplitude as a potential measure of urge to eat and predictor of food intake," Appetite. 2004;42:125-130.

van de Wall, Esther Henriette Eugenie Marie, "Capsaicin-Sensitive Nerves and Energy Homeostatis: Involvement in satiety and glucose homeostatis," Rijksuniversiteit Groniginen (Mar. 2005).

Pederson, J.F., "Sonographic Comparison of Gastric Emptying of Broth and Water: Is There a Promoting Cephalic Factor?" Acta Radiologica. 2005;46:132-134.

Powley, T.L., "Nutritional Implications of Cephalic Phase Responses: Vagal circuitry mediating cephalic-phase responses to food," Appetite. 2000;34:184-188.

Rogers, J. et al., "Cephalic phase of colonic pressure response to food," Gut. 1993;34:537-543.

Sengupta, J.N. et al., "Characteristics of Vagal Esophageal Tension-Sensitive Afferent Fibers in the Opossum," Journal of Neurophysiology. 1989;61(5):1001-1010.

Sobhani, Iradj et al., "Vagal Stimulation Rapidly Increases Leptin Secretion in Human Stomach," Gastroenterology. 2002;122:259-263.

Favretti, Franco MD et al., "Treatment of Morbid Obesity with the Transcend Implantable Gastric Stimulator (IGS): A Prospective Survey," Obesity Surgery. 2004;14(5):666-670.

Diaz Guemes, I et al., "Effect of subthreshold stimulation of vagal nerve on food intake pattern in swine," 9th Annual Conference of the International FES Society, Sep. 2004—Bournemouth, UK.

Konturek, S.J. et al., "Brain-Gut Axis and Its Role in the Control of Food Intake," Journal of Physiology and Pharmacology. 2004;55(1):137-154.

Sobocki, J. et al., "Microchip Vagal Pacing Reduces Food Intake and Body Mass," Hepato-Gastroenterology. 2001;48:1783-1787.

Forster, J. MD et al., "Gastric pacing is a new surgical treatment for gastroparesis," The American Journal of Surgery. 2001;182:676-681.

Krolczyk, G. et al., "Encoding Meal in Integrated Vagal Afferent Discharge," Journal of Physiology and Pharmacology. 2004;55(1):99-106.

Laskiewicz, J. et al., "Capsaicin Induced Deafferentation Enhances the Effect of Electrical Vagal Nerve Stimulation on Food Intake and Body Mass," Journal of Physiology and Pharmacology. 2004;55(1):155-163.

Travagli, R. Alberto et al., "Receptors and Transmission in the Brain-Gut Axis: Potential for Novel Therapies—V. Fast and slow extrinsic modulation of dorsal vagal complex circuits," Am J Physiol Gastrointest Liver Physiol. 2001;281:G595-G601.

Zhang, Lei et al., "Thermosensitive transient receptor potential channels in vagal afferent neurons of the mouse," Am J Physiol Gastrointest Liver Physiol. 2004;286:G983-G991.

Peles, Shachar et al., "Enhancement of antral contractions and vagal afferent signaling with synchronized electrical stimulation," Am J Physiol Gastrointest Liver Physiol. 2003;285:G577-G585.

Hinton, Elanor et al., "Neural contributions to the motivational control of appetite in humans," European Journal of Neuroscience. 2004;20:1411-1418.

NonFinal Office Action, mailed Mar. 31, 2009: Related U.S. Appl. No. 11/555,166.

Final Office Action, mailed Oct. 15, 2009: Related U.S. Appl. No. 11/555,166.

Advisory Action, mailed Dec. 17, 2009: Related U.S. Appl. No. 11/555,166.

NonFinal Office Action, mailed Oct. 23, 2012: Related U.S. Appl. No. 11/555,166.

Final Office Action, mailed Feb. 7, 2013: Related U.S. Appl. No. 11/555,166.

Notice of Allowance, mailed May 15, 2013: Related U.S. Appl. No. 11/555,166.

NonFinal Office Action, mailed Aug. 30, 2011: Parent U.S. Appl. No. 12/196,985.

Final Office Action, mailed Feb. 1, 2012: Parent U.S. Appl. No. 12/196,985.

Advisory Action, mailed Apr. 6, 2012: Parent U.S. Appl. No. 121196,985.

NonFinal Office Action, mailed Oct. 12, 2012: Parent U.S. Appl. No. 12/196,985.

Notice of Allowance, mailed Apr. 5, 2013: Parent U.S. Appl. No. 12/196,985.

* cited by examiner

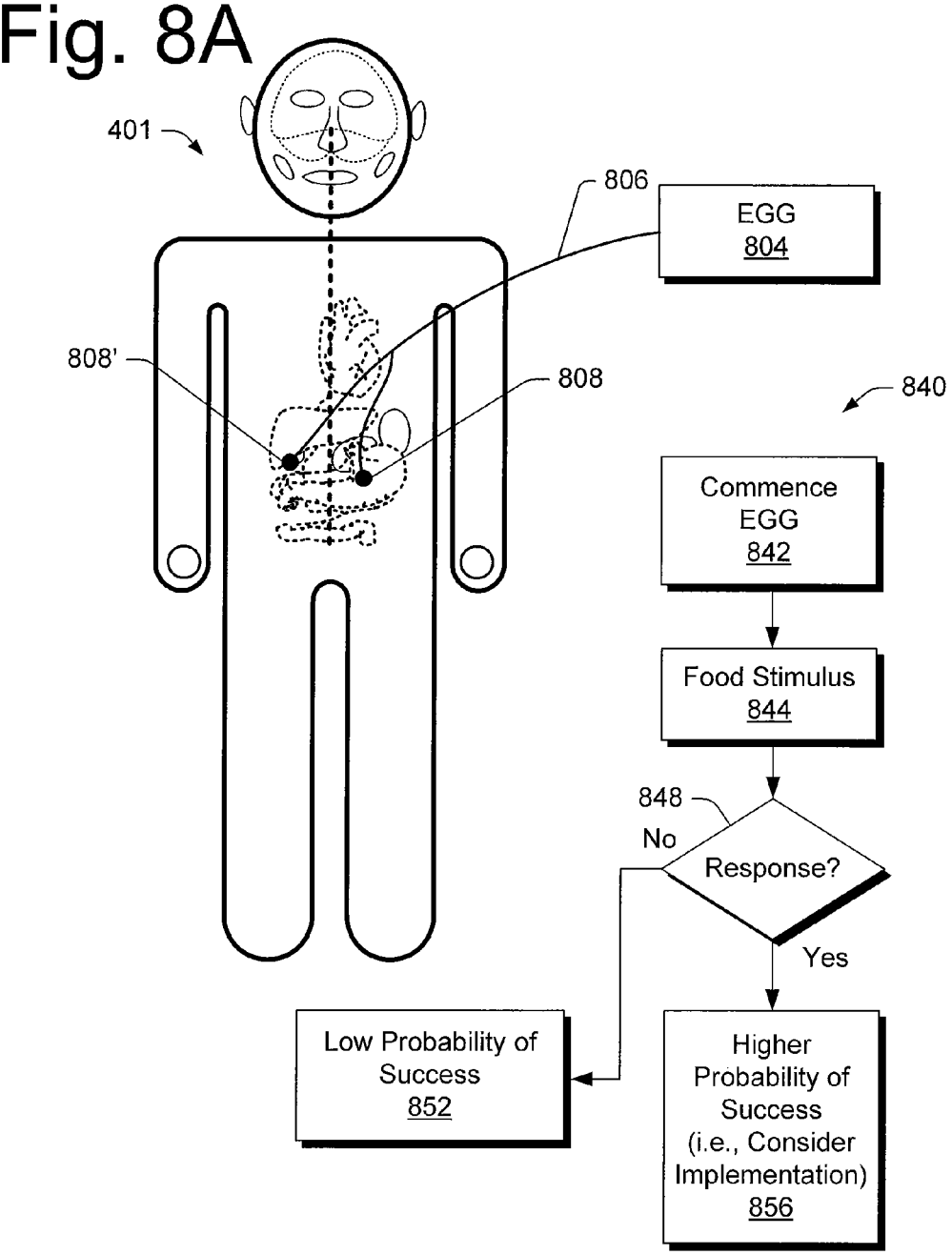

DETECTION OF FEEDING INTENT FOR USE IN TREATMENT OF EATING DISORDERS

CROSS-REFERENCE TO RELATED APPLICATIONS

This application is a continuation of copending U.S. patent application Ser. No. 12/196,985, filed Aug. 22, 2008, titled "Detection of Feeding Intent for Use in Treatment of Eating Disorders." This application is also related to copending U.S. patent application Ser. No. 11/555,166, filed Oct. 31, 2006, titled "Dual Therapy Electrical System for Treating Metabolic and Eating Disorders."

TECHNICAL FIELD

Exemplary methods, devices, systems, etc., presented herein generally relate to implantable electrical stimulation devices for sensing and/or altering food intake.

BACKGROUND

General Information on Food Intake

The human body normally functions in two states: food intake state and a fasting state. The duration and frequency of these states varies from individual to individual. Numerous factors are involved including availability of food as well as psychological and physiological condition.

Regarding food intake, nearly all of the body's energy comes from glucose and fatty acids. After being absorbed in the gastrointestinal tract (GIT), glucose can be taken up by cells and oxidized to generate ATP; linked with other glucose molecules and stored as glycogen; and combined with other glucose molecules and formed into fatty acids. Fatty acids, after being absorbed in the GIT can be oxidized to produce ATP or taken up by cells, combined with glycerol and stored as triglycerides. When a person has a positive energy balance, the hormone insulin plays a primary role in control of metabolic fuel metabolism. The pancreas secretes insulin in response to food intake. Insulin prepares the body for a sudden increase in metabolic fuels by facilitating glucose entry into cells for oxidation or storage. However, insulin inhibits release of fatty acids from fat cells. Absence of insulin (diabetes mellitus) leads to a buildup of blood glucose (hyperglycemia). Common diabetes disorders are type 1 where the body cannot produce insulin and type 2 where the body becomes less responsive to insulin.

Regarding fasting, the body normally relies on conversion of stored metabolic fuels. For example, the body breaks down glycogen and triglycerides to glucose and fatty acids. While the heart is a fatty acid burner, the brain relies on glucose. A group of hormones, sometimes referred to as counterregulatory hormones, mediate the breakdown and mobilization process. These hormones act, in general, counter to the actions of insulin and include epinephrine, glucagon and cortisol/corticosterone.

As discussed herein, various neural circuits control food intake and fasting hormones. Neural processes receive information, communicate information and respond to such information to thereby motivate the individual for food intake or not. While internal information affects such motivated behavior, at times, external information plays a role as well; thus, neural circuits that process internal and external information are involved.

As discussed in more detail below, mechanisms controlling food intake may include brain-based, peripheral-based and periphery to brain-based mechanisms. For example, inhibition of glucose oxidation in the caudal hindbrain increases food intake. Thus, the hindbrain, in contrast to the hypothalamus, contains cells that can monitor glucose availability and control food intake and epinephrine release. Peripheral mechanisms include those associated with the liver. Food passes through the liver where nutrients cause a decrease in food intake. In contrast, providing 2-deoxy-glucose (2DG) to the hepatic portal vein causes an increase in food intake. Information from the liver is conveyed to the brain via, for example, vagal pathways (vagotomy nulls these actions). Thus, a neuronal link exists between periphery and the brain. Perhaps the most complex mechanisms rely on hormones released from the periphery that act on the brain or peripheral organs.

Overall, a need exists for improved therapies to address disorders associated with food intake and metabolism. In particular, such improved therapies should aim to increase responder rate. In other words, a high probability of success should exist for a therapeutic system prior to implantation of the system. Various exemplary devices, methods, systems, etc., described below aim to provide for multiple therapies to address such issues.

SUMMARY

An exemplary method for treating obesity includes means for delivering electrical energy to a vagal nerve, means for detecting pre-prandial activity and, in response to the detection of pre-prandial activity, means for delivering electrical energy to the stomach to induce satiety. Various other technologies are also disclosed.

BRIEF DESCRIPTION OF THE DRAWINGS

Features and advantages of the described implementations can be more readily understood by reference to the following description taken in conjunction with the accompanying drawings.

FIG. 8A is a diagram of an exemplary arrangement for helping to decide whether a patient should be subject to particular therapy and FIG. 8B illustrates an exemplary method for helping to decide whether a patient should be subject to particular therapy.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Various exemplary methods, devices, systems, etc., disclosed herein pertain to sensing preprandial activity. Such information can be used for a variety of purposes. An exemplary method includes a pre-implantation assessment for an implantable device for altering food intake that relies, at least in part, on pre-prandial information. The pre-implantation assessment can allow for a higher response rate for therapies using such an implantable device.

Figure 1:
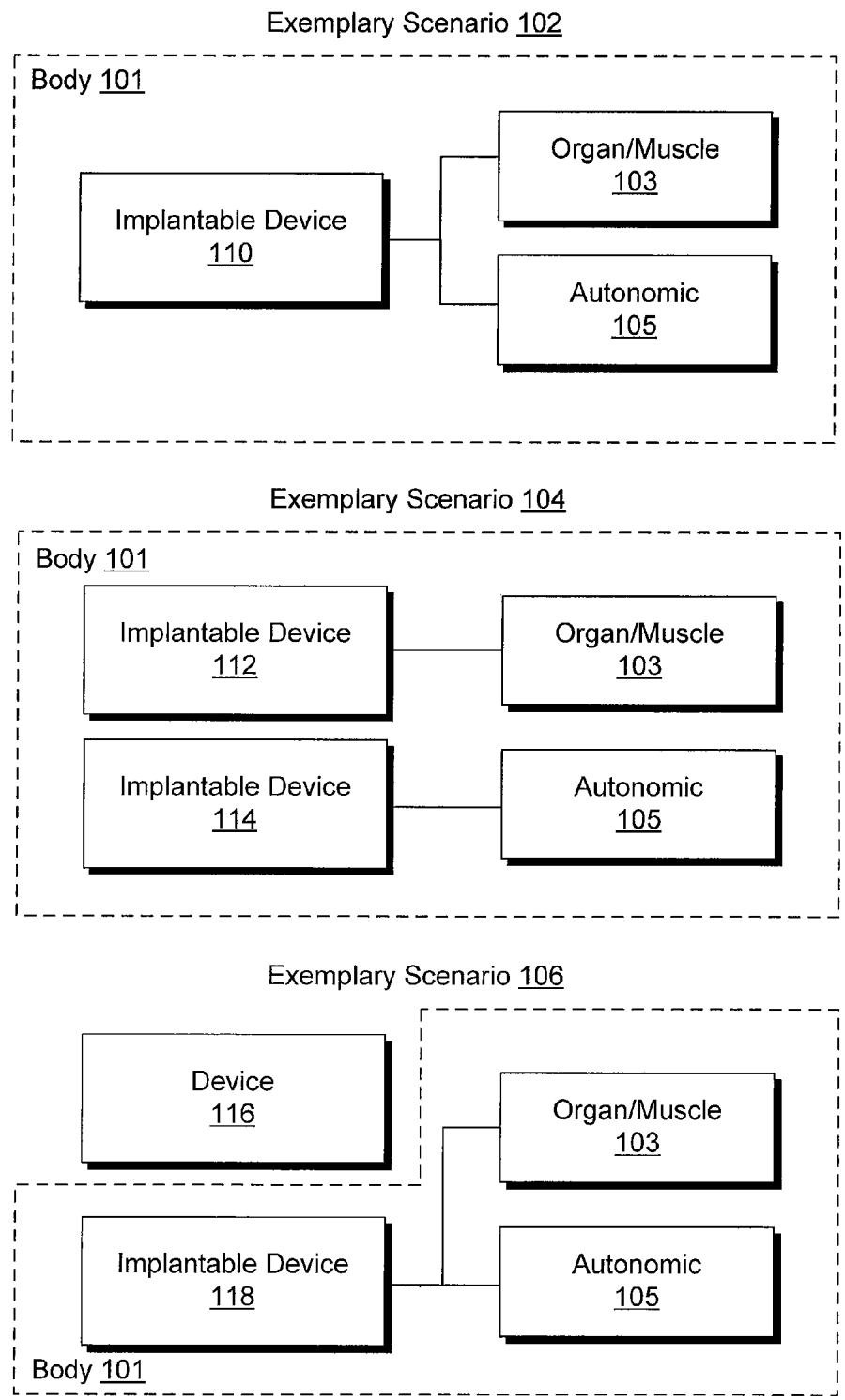
FIG. 1 is a diagram illustrating various exemplary scenarios where an implantable device interacts with organ/muscle and/or autonomic nerves in the body.

FIG. 1 shows various exemplary scenarios 102, 104 and 106 whereby at least one implantable device (e.g., 110, 112, 114, 118) interacts with an organ and/or muscle of the body 101 and/or interacts with the autonomic nervous system of the body 101. In general, such interactions include interactions that can adjust food intake or provide information relevant to food intake. An exemplary implantable device acquires pre-prandial information via its own sensing circuitry and/or communicating with another device that may be implantable or external to the body. An exemplary implantable device may optionally provide for cardiac therapy or communicate with a device that can provide for cardiac therapy. An exemplary implantable device may optionally provide for respiratory therapy or communicate with a device that can provide for respiratory therapy.

The exemplary scenario 102 includes a single implantable device 110 that can sense, activate and/or block activity of an organ and/or muscle 103 and/or activity of an autonomic nerve or nerves 105. With respect to food intake, the device 110 may acquire pre-prandial information and use such information to determine one or more parameters to stimulate a vagal afferent pathway and/or to stimulate stomach muscle in a manner that reduces food intake. As described in more detail below, an exemplary method implemented by the device 110 may acquire pre-prandial information using one or more electrodes or other sensors (e.g., chemical, mechanical, etc.) and then use the information to trigger stimulation of an organ/muscle 103 and/or autonomic pathway 105.

Such a method may act to conserve power of an implantable device, noting that such a device may be rechargeable or have a replaceable power source. A rechargeable device may rely on an external power source that transmits energy to charge a capacitor or other storage. With respect to power conservation, pre-prandial information may "wake" an implantable device and cause the device to delivery a therapy aimed at altering food intake. Such a method is optionally implemented in conjunction with one or more other therapies that may be triggered via other information or operate in a substantially continuous manner.

The exemplary scenario 104 includes two or more implantable devices 112, 114. In this example, the device 112 senses, activates and/or blocks activity associated with one or more muscles and/or organs 103. The other device 114 senses, activates and/or blocks activity of one or more autonomic nerves 105. In general, the devices 112, 114 operate in a coordinated manner to adjust food intake and/or to provide information relevant to food intake. The devices 112, 114 may include circuits to allow for uni-directional or bi-directional communication. Pseudo-communication may occur via a circuit in one of the devices that detects electrical or other actions of the other device. For example, where the device 112 delivers energy to the stomach, the device 114 may sense the electrical activity via one or more electrodes or other circuits. The device 114 may rely on such information to determine appropriate action (e.g., sensing, activating, blocking, alerting, communicating, etc.).

The exemplary scenario 106 includes an external device 116 and an implantable device 118. The external device 116 may acquire information from the implantable device 118 and/or acquire information about the body 101. For example, the external device 116 may acquire pre-prandial information and then communicate this information to the implantable device 118. In turn, the implantable device 118 may use the communicated information to determine an action related to one or more organs/muscles 103 and/or one or more autonomic nerves 105. In general, the device 118 is capable of delivering therapy aimed at adjusting food intake, for example, reducing food intake, regulating and/or scheduling food intake.

As described in more detail below, the external device 116 may acquire information via use of one or more body surface electrodes. For example, the external device may be capable of acquiring electromyographs that include pre-prandial information. Various studies indicate that skin conductance changes with respect to pre-pranidal action as well as autonomic tone. Thus, one or more body electrodes may be used to acquire skin conductance as an indicator of pre-prandial activity and/or autonomic tone.

Figure 2:
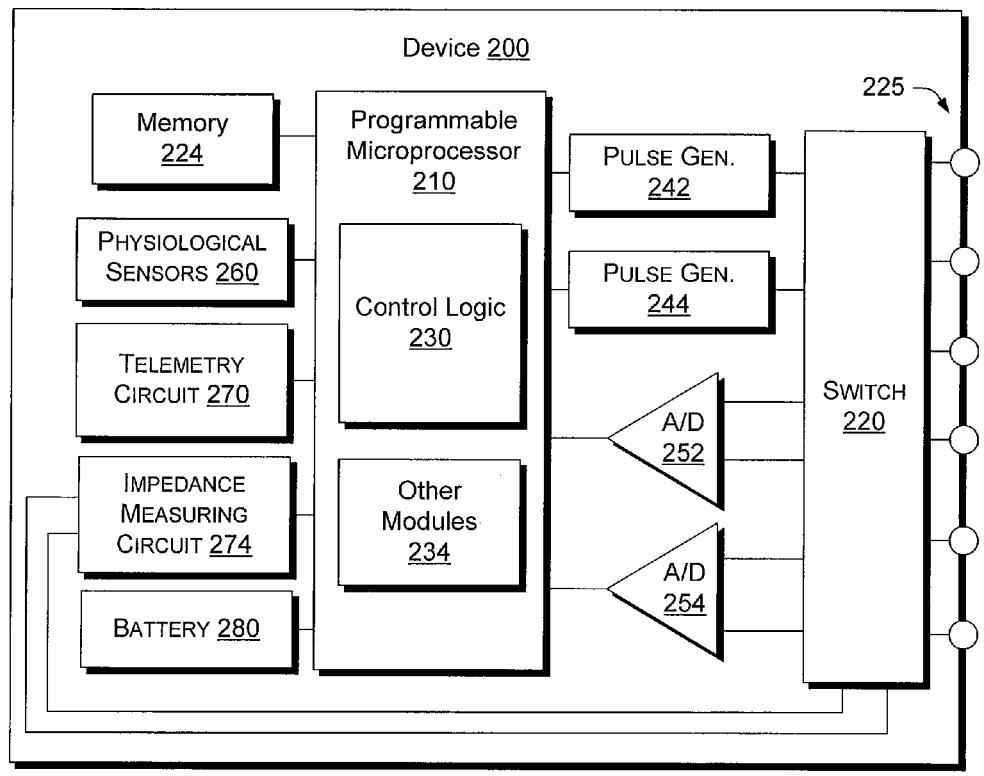
FIG. 2 is a functional block diagram of an exemplary implantable stimulation device illustrating basic elements that are configured to provide one or more therapies related to food intake.

FIG. 2 shows a block diagram of an exemplary device 200 capable of sensing, activating and/or blocking activity of any number of organs, muscles and/or nerves. A basic device may include a processor, memory, one or more inputs, one or more outputs and control logic stored as instructions in the memory and operable in conjunction with the processor. The device 200 includes various additional features.

The exemplary device 200 includes a programmable microprocessor 210 that can implement control logic 230 and other instructional modules 234. Information may be stored in memory 224 and accessed by the programmable microprocessor 210. For delivery activation energy, the device 200 includes one or more pulse generators 242, 244. The pulse generators 242, 244 may rely on a switch 220 for delivery of energy via one or more connectors 225. While a device may include one or more integral leads, in general, a device includes one or more connectors for connecting a lead or leads to the device. More particularly, the connectors 225 provide for electrically connecting one or more electrodes to the circuitry of the device 200. In the example of FIG. 2, the switch 220 may select an appropriate electrode configuration. An electrode configuration may include an electrode from one lead and an electrode from another lead, a case electrode and another electrode or electrodes from a single lead.

The device 200 further includes one or more analog to digital converters 252, 254 for converting analog signals to digital signals or values. The processor 210 may use a signal provided by one of the A/D converters 252, 254 to control a therapy or other process. A control signal from the processor 210 may instruct the switch 220 to select a particular electrode configuration for sensing electrical or other activity. As discussed below, various techniques include sensing nerve activity or other activity.

The device may include one or more physiological sensors 260. Such sensors may be housed within a case of the device 200 (e.g., a motion sensor), include a surface mounted component, include a lead, include a remote sensor, etc. A sensor may provide a digital signal or an analog signal for use by the processor 210 or other circuitry of the device 200. A physiological sensor may provide a signal via one or more of the connectors 225.

For purposes of communication with external or other implantable devices, the device 200 includes a telemetry circuit 270. The telemetry circuit 270 may include one or more antennae for transmission and/or receipt of electromagnetic signals. Such a circuit may operate according to a specialized frequency or frequencies designated for medical devices. Various conventional implantable devices rely on an associated programmer, which is an typically an external computing device with a communication circuit suitable for communicating with an implantable device for purposes of data transfer, status checks, software download, etc. Where the circuit 270 communicates with an implantable device or a device in electrical connection with a patient's body, then the body may be a conductive medium for transfer of information. For example, the circuit 270 may be capable of communication with a specialized wristwatch where the body is relied upon as a conductor.

The device 200 further includes an impedance measuring circuit 274. Such a circuit may rely on instructions from the processor 210. For example, the processor 210 may instruct the circuit 274 to provide a measured impedance for a particular electrode configuration. In such an example, the processor 210 may also instruct the switch 220 to provide the circuit 274 with a particular electrode configuration. Impedance information may be used by the processor 210 for any of a variety of purposes. The processor 210 may store impedance or other information to memory 224 for later use or for transmission via the telemetry circuit 270.

The device 200 includes a power source, which is shown as a batter 280 in the example of FIG. 2. The battery 280 powers the processor 210 and optionally other circuitry, as appropriate. In general, the battery 280 provides power to the pulse generators 242, 244. Consequently, the battery 280 provides for operation of circuitry for processing control logic, etc., and provides for energy to activate tissue. A lead-based sensor may connect to the device 200 via one or more of the connectors 225 and be powered by the battery 280. The battery 280 may be rechargeable, replaceable, etc.

While the device 200 includes particular features, various exemplary devices, systems, methods, etc., may use or be implemented using a different device with more or less features.

Figure 3:
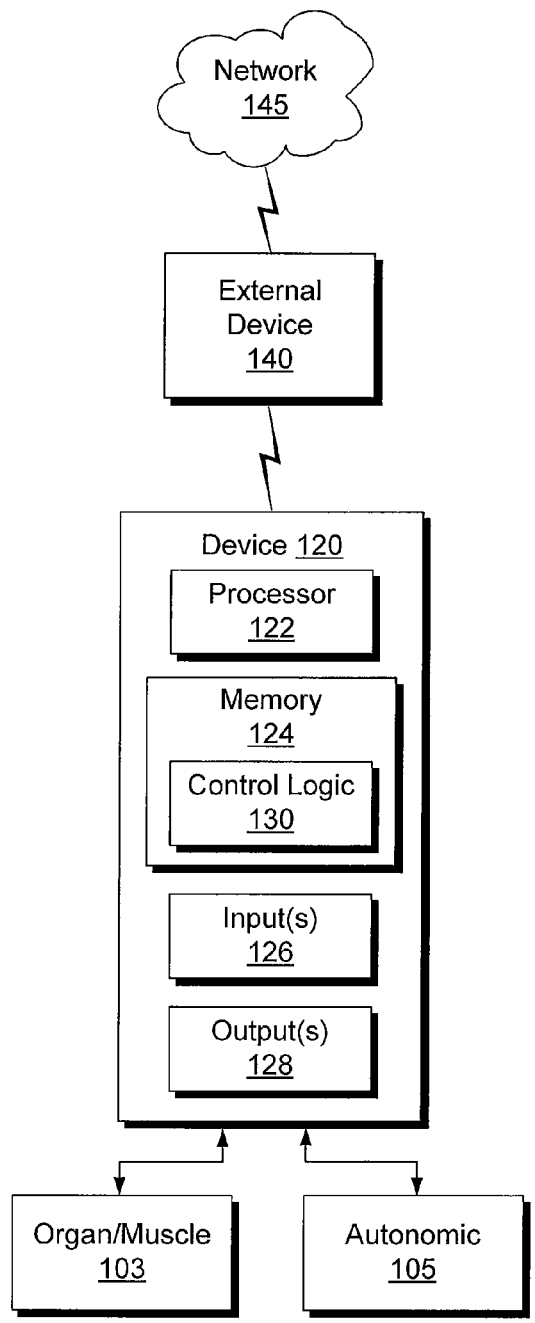
FIG. 3 is a block diagram of an exemplary arrangement of devices for use in delivering one or more therapies related to food intake.

FIG. 3 shows an exemplary arrangement 300 that includes an implantable device 120 in communication with an external device 140 which in turn is coupled to a network 145. The implantable device 120 includes a processor 122, memory 124, one or more inputs 126, one or more outputs 128 and control logic 130 stored as instructions in the memory 124 and operable in conjunction with the processor 122. The devices 120 and 140 may include uni-directional and/or bi-directional communication circuits.

An external device 140 includes one or more circuits to allow for uni-directional and/or bi-directional communication with at least one implantable device 120. The external device 140 is optionally in communication with a network 145 (e.g., intranet, Internet, etc.). The external device is optionally a device programmer.

The implantable device 120 can sense, activate and/or block activity associated with one or more organs and/or muscles 103 and/or activity associated with one or more autonomic nerves 105. For example, the device 120 may be an obesity therapy device that can deliver stomach muscle stimulation and optionally autonomic nerve therapy. in particular, the device 120 can acquire pre-prandial information and use such information to deliver an obesity therapy.

Coordinated operation of two or more implantable devices 120 may occur via the external device 140 and/or via communication between the devices 120 (uni-directional and/or bi-directional). In general, at least one of the implantable devices 120 pertains to a therapy that aims to acquire pre-prandial information and use such information to deliver an obesity therapy.

With respect to food intake therapies, the mechanisms are fairly complex and not all mechanisms are understood. As discussed below, evidence exists to support the existence of some mechanisms. However, an exemplary implantable device or devices may include learning algorithms whereby mechanisms are uncovered, utilized or otherwise better understood through use of various parameters for activation and/or blocking and/or through sensing activity associated with food intake or lack thereof and/or as a consequence of activating and/or blocking.

As described herein, an exemplary implantable device may acquire pre-prandial information or acquire information that is deemed to be pre-prandial by a care provider or other information, for example, as communicated to the implantable device by an external device.

Figure 4:
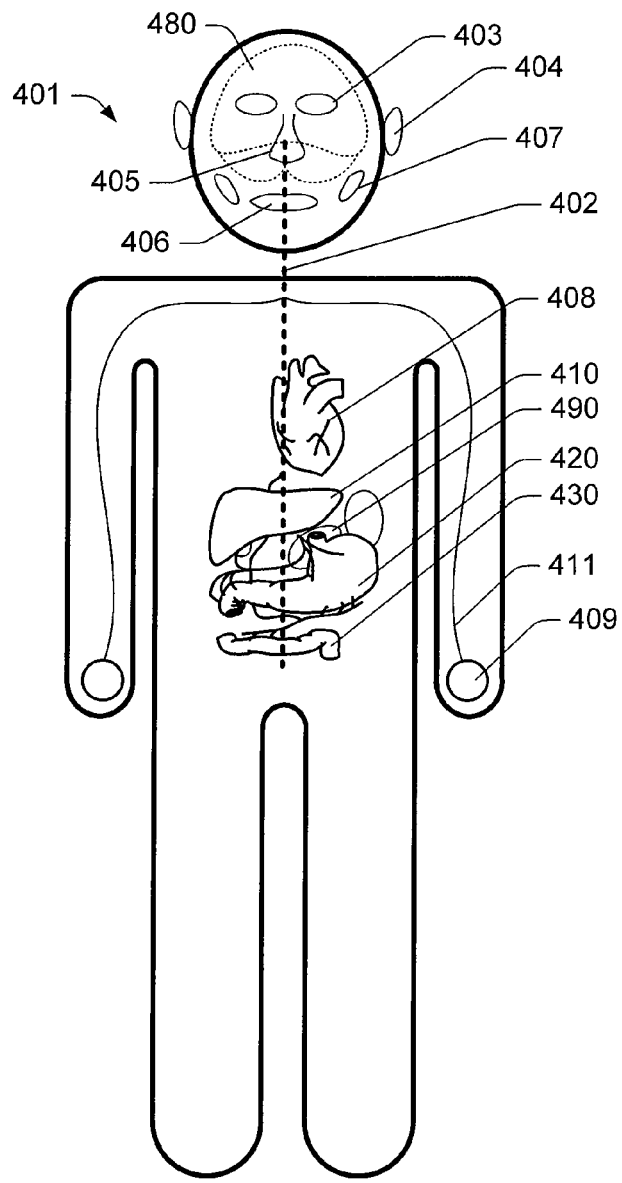
FIG. 4 is an approximate anatomical diagram of various organs and pathways associated with pre-prandial or cephalic phase responses to food stimuli (internal or external).

FIG. 4 shows a diagram 400 of various pre-prandial systems. An article by Mattes, "Physiologic responses to sensory stimulation by food: nutritional implications," J Am Diet Assoc. 1997 April; 97(4):406-413, provides a general overview of various processes related to pre-prandial or "cephalic phase" systems. As described herein, the term pre-prandial refers to a period just prior to food intake and to a period whereby intent to feed arises. The term cephalic phase refers to various physiological activities that include those initiated by thought (e.g., imagination, memory, etc.) and sensory receptors. For example, the cephalic phase includes thought initiated salivation as well as responses demonstrated by Pavlov, i.e., food can be a prompt and powerful stimulant to activate the digestive system. Pavlov also demonstrated that the vagus nerve is involved, which has many connections to the gastrointestinal tract (GIT).

The body 401 has many mechanisms associated with pre-prandial sensing, drive and action. The diagram 400 includes the brain 480, the spinal cord 402, the eyes 403, the ears 404, the nose (olfactory) 405, the mouth (feel, taste, etc.) 406, the salivary glands 407, the heart and circulatory system 408, the hands 409, the central nervous system 411, the liver 410, the stomach 420, the intestines 430 and the pancreas 490. Other organs involved and not shown include the lungs, the kidneys and the thyroid. Yet other body systems may be involved as well.

Consider that mere exposure to the sight, smell, taste, and textural attributes of foods elicits myriad digestive, endocrinologic, thermogenic, cardiovascular, and renal responses.

The responses are rapid (generally occurring within minutes of sensory stimulation), small (relative to the magnitude achieved when food is actually being metabolized), and transient (returning to near-baseline levels within minutes). Nevertheless, they have been hypothesized to prime the body to better absorb and use ingested nutrients. As discussed herein these are considered pre-prandial activity or cephalic phase responses.

With respect to specific responses, the aforementioned article by Mattes identifies the following cephalic phase responses: gastric, pancreatic exocrine, pancreatic endocrine, thermogenic, cardiovascular, and renal. A study by Nederkoorn et al., "Cephalic phase responses, craving and food intake in normal subjects," *Appetite*. August 2000; 35(1):45-55(11) showed that normal subjects do react to food exposure with changes in heart rate, heart rate variability (HRV), salivation, blood pressure, skin conductance and gastric activity. A subsequent study by Nederkoorn et al., "Cue reactivity and regulation of food intake," *Eat Behav*. 2002 Spring;3(1):61-72, showed that unrestrained eaters exhibited an increase in heart rate, gastric activity, and saliva during food exposure while restrained eaters did not. Yet another study by Nederkoorn et al., "Exposure to binge food in bulimia nervosa: finger pulse amplitude as a potential measure of urge to eat and predictor of food intake," *Appetite*. April 2004; 42(2): 125-130, showed that finger pulse amplitude as a potential measure of urge to eat and predictor of food intake. A study by Barkeling et al (2003) examined obese subjects that ate 24% less food when blindfolded.

As already mentioned, Pavlov's famous studies indicated involvement of the parasympathetic nervous system. A study by Powley, "Vagal circuitry mediating cephalic-phase responses to food," *Appetite*, April 2000; 34(2):184-188, reported that the dorsal vagal complex in the medulla oblongata is the hub of the central nervous system network that produces vagal cephalic-phase reflexes. This study noted that the dorsal vagal complex receives input both from exteroceptive senses, such as olfaction and vision, and from forebrain areas that modulate reflex strength. Various vagal pathways and brain mechanisms are discussed in more detail below.

Known physiological events that occur during the cephalic phase include increased gastric secretion (e.g., decrease in pH), increased efferent vagal traffic, increase in gastric motility as well as receptive accommodation or relaxation of the fundus. Various techniques exist for determine that a person is entering the cephalic phase. For example, drop in intra-gastric pH; efferent vagal traffic via vagus nerve sensing and signal analysis; increase in gastric motility via sensing of the myoelectrical activity of the GIT (e.g., stomach wall); and receptive accommodation via detecting distention of the fundus by tension sensors, impedance sensors or pressure sensors imbedded within the gastric wall or lumen. Prior to a discussion of such techniques, a general discussion of food intake and related mechanisms follows. Such a discussion is helpful in appreciating a distinction between pre-prandial or cephalic phase and subsequent food intake or digestive phases. Further, such a discussion is helpful to understand better therapies that may be delivered by an implantable device.

Figure 5:
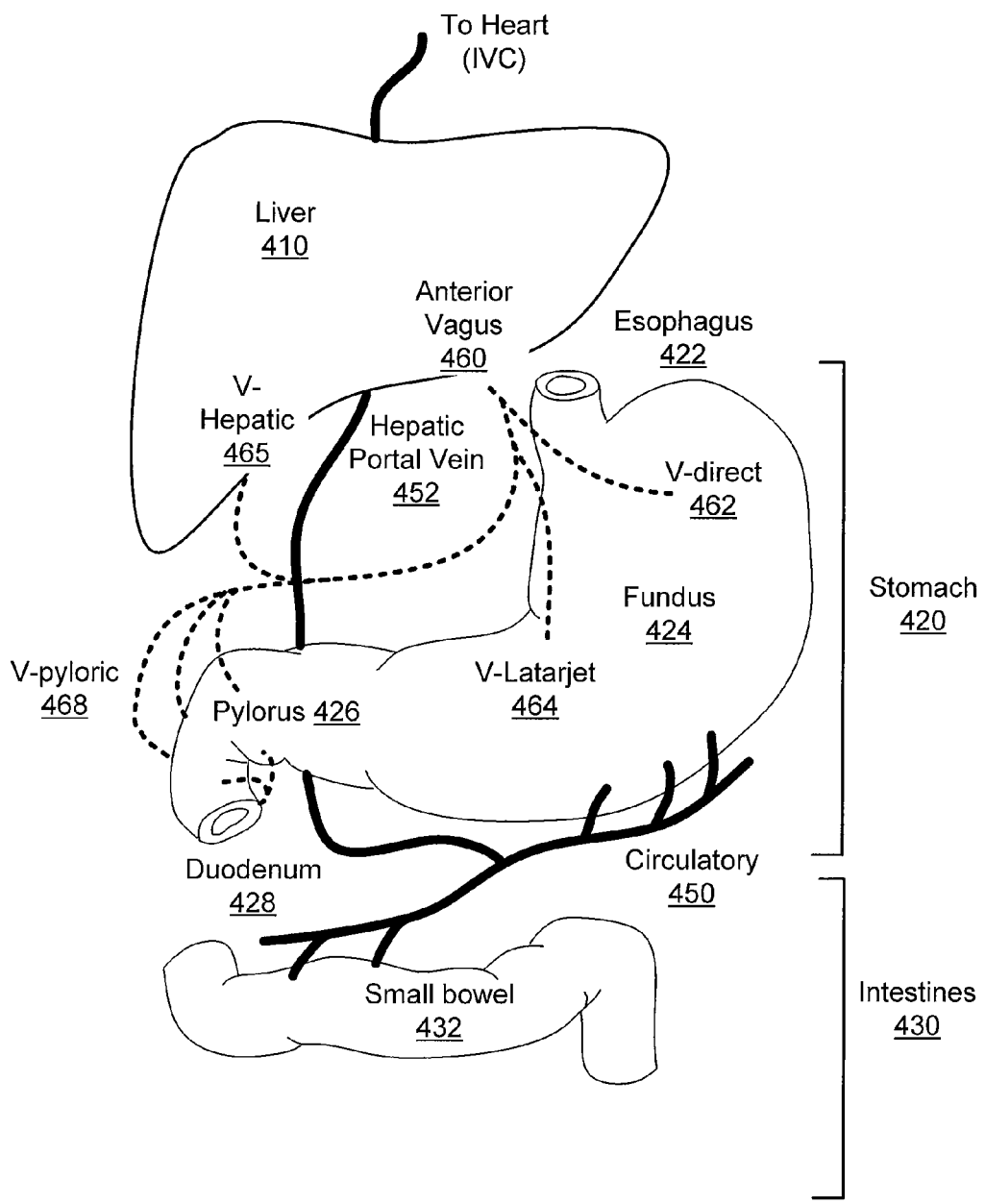
FIG. 5 is an approximate anatomical diagram of various organs and pathways.
Figure 6:
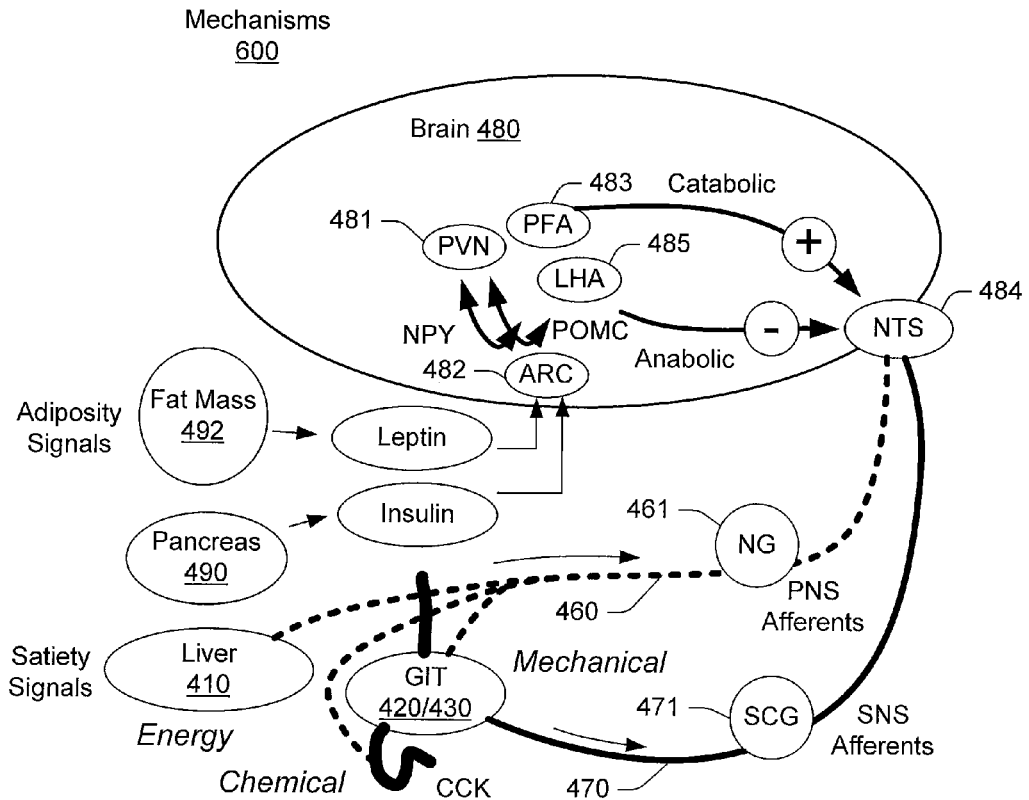
FIG. 6 is a diagram of various mechanisms and pathways associated with food intake (including intent to feed).

FIG. 5 is an anatomical diagram 500 of various sub-thoracic organs, nerves and circulatory routes 450. FIG. 6 is a diagram 600 that shows various neural circuits related to organs and the brain. The discussion that follows refers to the diagrams 500 and 600 of FIGS. 5 and 6, respectfully. The exemplary devices of FIGS. 1, 2 and 3 optionally sense activity of and/or activate various mechanisms discussed with respect to FIG. 4 or FIGS. 5 and 6 below. Exemplary methods follow that pertain to some non-exhaustive examples.

General Nervous System (Brain-Gut—CNS/Autonomic/ENS)

Various studies refer to a "brain-gut axis" as a primary mechanism for control of food intake. A review by Konturek et al., "Brain-gut Axis and Its Role in the Control of Food Intake," *J. Physiol. Pharma*. 2004; 55(1):137-154, recognizes that the gastrointestinal tract (GIT) interacts with the central nervous system (CNS) and the enteric nervous system (ENS) where the CNS and ENS form the brain-gut axis.

The ENS includes specific innervations and plexuses associated with the GIT. For example, the GIT includes a myenteric plexus known as the Auerbach plexus and a submucous plexus known as the Meissner plexus. These plexuses are primarily associated with parasympathetic aspects of the autonomic nervous system. The Auerbach plexus is located between the longitudinal and circular layers of muscle in the tunica muscularis (generally from pylorus 426 to duodenum 428) and relates to tonic and rhythmic contractions. The Meissner plexus is buried in the submucosa and relates to epithelial cell function and GIT blood flow. Another plexus, the coeliac plexus, is associated primarily with sympathetic aspects of the autonomic nervous system.

As already inferred, interactions exist between these ENS plexuses and the autonomic nervous system, in particular, a vagal pathway and a splanchnic path exist between the CNS and the ENS. The parasympathetic vagal pathway includes cholingeric nerves (about 80% to 90% unmyelinated C-fibers) while the sympathetic splanchnic pathway includes noradrenergic nerves. Regarding interactions, consider that the Valsalva maneuver, commonly associated with parasympathetic activation, as well as increasing intraabdominal pressure (e.g., squat position) can increase normal defectation.

With respect to more specific routes of autonomic innervation, studies indicate that the left vagus supplies efferent preganglionic fibers mainly to the anterior surface of the stomach and that the right vagus supplies efferent preganglionic fibers mainly to the posterior surface of the stomach. For example, the diagram 500 of FIG. 5 shows the anterior vagus 460 as it tracks from the esophagus 422 to the liver 410, the stomach 420 and the intestines 430. In addition both vagi send branches to the coeliac plexus; however, the degree of interaction with the primarily sympathetic coeliac plexus is suggested to be minimal. The parasympathetic preganglionic vagal fibers penetrate the layers of the gastric wall, to form synapses in the ganglion cells of the Auerbach plexus and in the Meissner plexus. Postganglionic fibers emerge from the plexuses and supply musculature and mucosa.

The coeliac plexus, also known as the solar plexus, is a junction for autonomic nerves supplying the upper abdominal organs (liver, gall bladder, spleen, stomach, pancreas, kidneys, small bowel, and about two-thirds of the large bowel). The coeliac plexus receives sympathetic nerves from the greater splanchnic nerve (around T5/6 to T9/10 vertebrae), the lesser splanchnic nerve (around T10/11 vertebrae) and the least splanchnic nerve (around T11/12 vertebrae). As already mentioned, the upper abdominal organs receive their parasympathetic supply from the left and right vagal trunks which pass through the coeliac plexus without any known significant interaction.

Brain-Gut Axis

The brain-gut axis also relies on afferent signals from the GIT and other organs. Afferent signals from the upper GIT are transmitted by the vagi, splanchnic mesenteric nerves, and pelvic afferents. Together, these afferent nerves provide the peripheral extrinsic neural part of the gut-brain axis. The upper GIT is largely innervated by vagal afferents; the pelvic afferents are limited to the lower or large bowel, while splanchnic afferents innervate much of the GIT. The intrinsic, enteric neural systems such as the myenteric and submucosal plexuses (Auerbach and Meissner) may mediate between GIT mucosal and muscular events and extrinsic neural signaling.

The vagus nerve consists of both sensory and motor axons. In the periphery, as already mentioned, the vagus enters the abdomen with two trunks (the right, dorsal or posterior and the left, ventral or anterior) that track generally along the esophagus. When the vagi cross the diaphragm, in most individuals they divide into five distinctive branches: (i-ii) paired gastric branches, (iii-iv) paired celiac branches and (v) a single hepatic branch that originates from the ventral trunk.

The diagram 500 of FIG. 5 shows various gastric branches of the anterior vagus 460. In particular, the diagram 500 includes direct branches 462 to the fundus 424 (V-direct), pyloric branches 468 to the pylorus 426 (branches emanating from vagal supply to liver 410 that include superior pyloric nerves and inferior pyloric nerves), a hepatic branch or branches 465 (V-hepatic) and the anterior nerve of Latarjet 464 (V-Latarjet, principal anterior nerve of lesser curvature of the fundus 424). Again various branches are linked to the aforementioned Auerbach plexus and Meissner plexus.

The diagram 600 of FIG. 6 shows a more general representation of the anterior vagus 460 as it tracks to the brain 480. As already mentioned, the vagus includes primarily C-fibers. Ingestive and visceral reflexes are mediated by nociceptive or chemosensitive C-fibers which have their cell bodies in the nodose ganglia 461 and show a viscerotopic distribution in the nucleus of the solitary tract 484 (NTS) of the brain 480.

Evidence based on anterograde tracing after injections into the individual subdiaphragmatic vagal branches show discrete, yet somewhat overlapping, NTS 484 termination fields for each vagal branch. Thus, the NTS 484 contains viscerotopic and at least some information specific to a particular vagus branch. As already discussed, the hepatic branch 465 of the anterior vagus 460 includes branches that supply other regions. While pyloric branches 468 and fundus branches 462, 464 are shown in the diagram 500 of FIG. 4, other branches also exist (e.g., antrum, duodenum, and caecum), which is consistent with the general notion that individual gut vagal branches innervate multiple GIT segments. Thus, as with the aforementioned efferent innervation of the GIT, a gastrointestinal target can be innervated by vagal afferents from more than one gut vagal branch.

While various exemplary techniques discussed herein focus on afferent nerves, such techniques optionally sense, activate or block efferent nerve activity. Various efferent nerves project from the dorsal or posterior motor nucleus of the vagus (DMN), a structure just anterior of the NTS 484. The DMN contains numerous dendrites penetrating the NTS and the Area Postrema (AP). About 95% of preganglionic neurons in the DMN contribute to projections to the stomach suggesting that the efferent part of the vagus nerve is highly involved in the motor innervation of the stomach.

Again, as already mentioned, the posterior vagus appears to have more efferent character while the anterior vagus appears to have more afferent character with respect to the GIT. Hence, as in the afferent projections, each vagal branch contains the axons of a topographically distinct column of cells within the DMN. Therefore, the afferent-efferent viscerotopic and branch specific organization of the vagus likely reflects distinct neurophysiological reflexes and functions involved in ingestion. Such an organization may be used to further the goals of various exemplary techniques discussed herein.

Vagal afferents appear to be sensitive to a variety of stimuli. Different populations of vagal afferents with terminations in the GIT indicate different sensory modalities, for example, reaction to mechanical as well as chemical stimulation. More specifically, vagal endings in the longitudinal and circular muscle layers are also defined as intramuscular arrays (IMAs) and have been suggested to be in-series tension receptors (e.g., mechanical sensors).

Vagal afferents in the myenteric plexus (Auerbach) throughout the GIT are called intraganglionic laminar endings (IGLEs) and exhibit characteristics of a tension receptor. Thus, evidence indicates that vagal afferent fibers play a role in volume detection of the stomach and gut, which may contribute to the process of satiation. This role is supported by neurophysiological studies that link the vagus to the process of satiation and meal termination. Various exemplary techniques discussed herein optionally include sensing, activating and/or blocking vagal afferent fibers associated with the myenteric plexus (Auerbach) to thereby affect food intake of an individual.

As can be appreciated, a variety of chemical messengers exist that play a role in food intake. The diagram 600 of FIG. 6 shows various structures and refers to some messengers. Such messengers include ghrelin (from stomach 420), leptin (from fat mass 492), insulin (from pancreas 490), cholecystokinin (from small intestine 432), peptide YY (from intestines 430), melanotropin (from arcuate nucleus 482), agouti-related peptide (from arcuate nucleus 482), neuropeptide Y (from arcuate nucleus 482). Some details are discussed below for some of these chemical messengers.

Ghrelin

Ghrelin is an endogenous ligand for the growth hormone secretagogue receptor (GHS-R) located in the anterior pituitary and it is the only identified gut hormone (produced in the stomach 420) that stimulates appetite and food intake. Plasma ghrelin concentrations rise immediately before food intake and fall postprandially. Intravenous ghrelin suppresses vagal afferent signaling while vagal efferent signaling participates in the starvation-induced rise in ghrelin. This effect is abolished by vagotomy in rats without affecting the usual postprandial decline in baseline plasma ghrelin concentrations, suggesting separate pathways. Various exemplary methods disclosed herein optionally include sensing, activating and/or blocking of vagal afferent nerves and/or vagal efferent nerves to thereby affect food intake.

Circulating ghrelin is also involved in central appetite regulation and energy balance. Intracerebroventricular (ICV) ghrelin stimulates neuropeptide Y (NPY) and agouti related protein (AgRP) neurons in the hypothalamus and ICV administration of ghrelin in rats decreases latency after the first meal and results in hyperphagia from increased meal frequency rather than meal size. These findings suggest that circulating ghrelin functions to initiate meals.

Fasting plasma ghrelin is significantly lower in obese subjects and negatively correlates with body mass index, percent body fat, fasting insulin and leptin (possibly a physiological adaptation to the long-term positive energy balance associated with obesity). During dieting, increases in ghrelin concentration correlate with the extent of weight loss. Ghrelin may contribute to the difficulty in maintaining diet-induced weight loss because obese patients lack the normal postprandial decline in plasma ghrelin level.

A proposed obesity therapy uses rimonabant, a CB1 receptor antagonist, which has been shown to decrease plasma ghrelin in fed rats and suppress the preprandial rise in ghrelin in fasting rats. Various exemplary techniques disclosed herein optionally include drug therapy whereby administration of a drug such as, but not limited to, rimonabant.

Another potential obesity drug is MK-677, a synthetic ligand for GHS-R that has been shown to impair oral glucose tolerance when administered orally to obese males. Altered ghrelin levels after RYGB may contribute the reversal of insulin resistance through an effect at GHS-R. Further studies are needed to determine whether MK-677 has feeding-altering ability similar to that of ghrelin.

Leptin

Leptin (Greek leptos, meaning thin) is produced by white adipose tissue (e.g., fat mass 492) and conveys information to the hypothalamus and hindbrain as to energy stored in fat. Leptin acts to suppress appetite, affect energy expenditure and regulate euroendocrine function and metabolism.

Low-dose leptin in humans reverses the thyroid hormone suppression associated with maintaining a 10% weight loss, which demonstrates that secretion of thyroid hormones may be related to plasma leptin concentrations during periods of weight loss and maintenance.

Leptin inhibits the stress-responsive secretion of the hypothalamus-produced corticotropin releasing hormone (CRH) in mice and is postulated to lead to CRH receptor up-regulation, a finding that correlates with the enhanced secretion of ACTH (the hormone that triggers cortisol secretion from the adrenal glands) by the pituitary gland, which is a response associated with insulin resistance in obese subjects given CRH.

Obese people have elevated circulating leptin levels where the more obese, the higher the level. Leptin resistance is thought to play a role in obesity. Low levels of circulating leptin may provide a signal that acts to prevent starvation. Again, the human body has more mechanisms to prevent starvation than to prevent obesity.

Insulin

The beta cells of the Islets of Langerhans of the pancreas 490 produce insulin. Circulating insulin levels increase upon food intake and are proportional to body fat. Insulin promotes transport of glucose from the circulatory system into tissues, stimulates uptake of glucose and deposition of glycogen in the liver 410, decreases release of glucose by the liver 410, decreases food intake and increases energy expenditure via action on the hypothalamus and/or hindbrain.

Cholecystokinin

Cholecystokinin (CCK) acts as a satiety hormone and is produced by a population of I cells (mucosal endocrine cells) in the small intestine 432 by presence of nutrients in the duodenum. Evidence indicates that CCK and the vagal action are intimately linked. CCK is known to induce satiety after peripheral administration whereby vagal afferents 460 are required for the effects of CCK on food intake (ablation of these vagal afferents 460 by systemic capsaicin treatment abolishes the action of CCK). CCK receptors to induce satiation exist on vagal afferents 460 and in the nodose ganglion 461. Various exemplary techniques discussed herein optionally include sensing, activating and/or blocking vagal afferents 460 as they relate to absence or presence of CCK to thereby affect food intake.

Evidence gained through administration or examination of CCK suggests that vagal afferents 460 are involved in the long-term regulation of energy homeostasis. For example, when rats maintained on a high fat diet are exposed to increased levels of endogenous CCK, they show a reduced sensitivity to exogenous CCK.

Various studies indicate that stimuli related to food intake (such as mechanical distension, chemical composition of luminal contents, gut peptides and neurotransmitters) can be sensed by vagal afferents 460 and thereby play a role in satiation and meal termination. Vagal afferents 460, receptive to CCK, may play an indirect role in the long-term regulation of energy balance. Various exemplary techniques disclosed herein optionally sense, activate and/or block vagal afferent activity to thereby affect long-term regulation of energy balance.

With respect to mechanical effects, pyloric cuff experiments and sham feeding preparations support the proposition that the stomach 420 detects volume. Hungry animals eat significantly longer and more when the food is drained from the stomach 420. Likewise, when rats eat a very large meal or receive gastric preloads with occlusion of the pyloric cuff rats eat less than with the cuff open. In addition, a study showed that saline was as effective as a liquid diet to induce satiation when gastric emptying was prevented by pyloric cuffs, which indicates that the stomach 420 is primarily involved in volume detection. Such a finding is confirmed by the observation in humans that reduction of stomach capacity by banding is often used to treat severe obesity.

With respect to digestion processes, most absorption and enzymatic activity occurs in the small intestine 432. Humoral factors involved in the process of satiation are also secreted by the small intestine 432 (e.g., CCK); hence, the small intestine 432 is thought to be primarily involved in nutrient sensing. Some vagal afferents 460 respond to infusions of specific nutrients as carbohydrate, fatty acids or amino acids. Thus, vagal afferents 460 innervating the small intestine 432 are able to respond to different nutrients. There are indications that specific nutrients may be sensed by anatomically distinct populations of visceral afferent neurons 460.

In a normal meal, gastric stimulation occurs simultaneously with intestinal stimulation. Therefore, it is likely that these responses are modulated by humoral factors of the duodenum (e.g. CCK) and the stomach 420 (e.g. leptin and grehlin).

Other Factors

Other chemical messengers include neuropeptide Y (increase food intake), AgRP (increase food intake and a-MSH antagonist) and a-MSH (inhibit food intake).

PYY is one of a family of peptides, including NPY and pancreatic polypeptide (PP), a hormone secreted postprandially from the PP cells of the islets of Langerhans of the pancreas 490. The endogenous forms of PYY (PYY1-36 and PYY3-36) are synthesized by the GIT 420/430 and released into the circulation after a meal. PYY3-36 infusion in obese and lean subjects induces a similar inhibition of appetite and food intake, resulting in reduced cumulative 24-hour food intake.

Serotonin is an important ENS neurotransmitter and paracrine hormone. Some 95% of the body's serotonin is expressed in the GIT 420/430, most of which is released by its entrochromaffin epithelial cells in response to luminal pressure (intrinsic peristaltic reflex), vagal stimulation, nociception (nociceptive reflex), and other chemical signals. Autonomic nervous system efferents modulate ENS-initiated changes in gut motility, altering nutrient absorption based on small bowel transit time.

Brain Structures

With respect to the role of the brain 480, many have focused on the arcuate nucleus of the hypothalamus 482 (ARC) and the paraventricular nucleus of the hypothalamus 481 (PVN). Many have hypothesized that circulating ghrelin, leptin and insulin act in the ARC 482 to signal the status of body energy available. Arcuate neurons producing a-MSH or NPY/AgRP project to neurons in the vicinity of the PVN 481 and, in response, food intake and energy expenditure are adjusted. However, details of specific mechanisms remain unknown. The role of insulin has been doubted as playing being major, the role of leptin is unresolved, lesions on ARC 482 have little effect on energy balance and NPY or AgRP gene knock-out have little effect either. Some have begun to focus more on the hindbrain. In any instance, mechanisms appear to be complex and to some extent redundancies exist. The existence of redundancies indicates that a desired result may be achieved in one or more manners.

While mechanisms remain to be detailed, it is without a doubt that various mechanisms allow for communication of information from the GIT 420/430 to the brain 480. Nutrients stimulate chemoreceptors in the GIT 420/430, pancreas 490, and liver 410, whereas bowel distention stimulates vagal afferents 460 and mechanoreceptors. Glucose-sensitive cells exist within the NTS 484 and ARC 482.

As already mentioned, chemical and pressure changes in the GIT 420/430 are transmitted via vagal afferents 460 to the NTS 484. Evidence indicates that nutrients simultaneously stimulate enteroendocrine cells to secrete appetite regulatory hormones, including CCK from 1 cells in the duodenum and jejunum, PYY and glucagon-like peptide-1 (GLP-1) from L cells primarily in the ileum and colon, glucose-dependent insulinotropic polypeptide (GIP) from K cells in the duodenum, and ghrelin from oxyntic cells (XUA-like cells in rodents and P/D1 cells in humans) primarily in the fundus 424.

CCK secreted during meals acts as a paracrine hormone at CCK1 receptors on mechanosensitive vagal afferents 460 located primarily in the pyloric sphincter and proximal duodenum (e.g., V-pyloric 468). CCK is thought to induce short-term satiety by sensitizing vagal mechanoreceptors to gastric and duodenal distention. CCK is also thought to decrease meal size by inhibiting gastric emptying, thereby augmenting the nutrient preload sensed by vagal afferents 460 and the NTS 484. NTS 484 pro-opiomelanocortin (POMC) neurons are activated by intraperitoneal injections of CCK in mice, and melanocortin 4 receptor (MC4R) expression is required for CCK-induced suppression of food intake.

The thyroid also plays a role in metabolism. Thyroid hormones enhance the effects of norepinephrine, increasing basal metabolic rate, thermogenesis, and lipolysis. Low-dose leptin in humans reverses the thyroid hormone suppression associated with maintaining a 10% weight loss, which demonstrates that secretion of thyroid hormones may be related to plasma leptin concentrations during periods of weight loss and maintenance.

The sympathetic nervous system also plays a significant role in the regulation of energy balance, and there is evidence of its dysfunction in obese persons. Analysis of heart rate variability in obese subjects suggests an increase in basal sympathetic activity and sympathetic response to cold exposure is blunted in obese subjects. Referring to the diagram 600 of FIG. 6, a sympathetic, splanchnic pathway 470 connect to the brain 480 via a superior cervical ganglion 471. The sympathetic pathway 470 can provide afferent information to the NTS 484. The diagram 600 also shows the periformical area (PFA) 483 and lateral hypothalamus area (LHA) 485 as playing a role in metabolic mechanisms.

Vaso-Vagal Reflexes

The aforementioned term "gut-brain axis" refers to the observation that most visceral primary afferents have their nerve endings in the dorsal or posterior vagal complex of the hindbrain. The process of satiation appears to be controlled by a reflex mechanism known as vago-vagal reflexes, noting that forebrain structures are not required for the inhibition of food intake (decerebrated rats still show satiation to food and injection of CCK). In other words, visceral feedback from the GIT tract to brainstem areas is sufficient to induce satiation. More broadly, vaso-vagal reflex circuits in the medulla are responsible for the smooth coordination of the digestive processes carried out from the oral cavity to the transverse colon.

A study by Travagli et al., "Receptors and Transmission in the Brain-Gut Axis: Potential for Novel Therapies: V. Fast and slow extrinsic modulation of dorsal vagal complex circuits," *Am J Physiol Gastrointest Liver Physiol* 2001; 281:G595-G601, focused on extrinsic modulation of these vago-vagal reflex circuits, with a particular emphasis on modulation by "fast" classic neurotransmitters and by "slow" neuromodulators.

A dissertation by van de Wall, "Capsaicin-sensitive nerves and energy homeostatis: Involvement in satiety and glucose homeostasis," Rijksuniversiteit Groniginen (March 2005), details various vagal afferent pathways and mechanisms.

While various GIT hormones can effect significant changes in GIT function by acting on vagal afferents, studies suggest that GIT hormones can also exert control over digestion by acting directly on neurons of the dorsal vagal complex, for example, to control vagal efferent outflow to the viscera. Further, chemical messengers produced by the immune system can also affect function of neurons of the gastric vago-vagal reflex control circuit.

Electrical Stimulation of Vagal Pathways

With various relationships between vagal pathways and food intake having been established or inferred, some researchers have studied electrical stimulation of these pathways. For example, a study by Sobocki et al., "Microchip vagal pacing reduces food intake and body mass," *Hepato-gastroenterology* 2001;48:1783-1787, relied on use of microchips to stimulate the vagal afferents in a rabbit model whereby the results suggested that reduced activity of vagal afferent fibers could be involved in weight gain.

Another study applied the findings of Sobocki et al. to a swine model, Diaz Guemes et al., "Effect of subthreshold stimulation of vagal nerve on food intake pattern in swine," 9th Annual Conference of the International FES Society September 2004, Bournemouth, UK. This study pointed to the bigger size of the porcine ventral vagal trunk and noted that the electrical impulses applied to the vagal nerve for the both studies were constant in voltage. The researchers stated that because the intensity of the impulses varies according to the nerve diameter (according to Ohms Law) in both species, different fibers may perform different functions when being stimulated in each species using the same stimulation parameters (also noting that stimulation subthreshold may be lower in fast conducting fibers than in slow ones).

While certain vagal nerve stimulation parameters provoked a decrease in body weight and food intake in rabbits, these proved to be subthreshold for changing food intake pattern in pigs, yet, increased systemic gastrin and insulin. Sobocki et al. noted that such findings have been reported by others, referring to a study that applied vagal stimulation with parameters of 13.5 mA, 10 Hz, 5 msec, 10 min to stimulate insulin secretion in dogs and two other studies whereby vagal stimulation increased gastrin concentration. The study of Sobocki et al. concluded that vagal nerve stimulation using parameters that reduced food intake in rabbits was not enough to provoke changes in short term ingestive behavior in swine, but stimulated insulin and gastrin secretion.

Other studies have used electrical vagal nerve stimulation to better understand mechanisms of food intake. For example, a study by Laskiewicz et al., "Capsaicin induced deafferentation enhances the effect of electrical vagal nerve stimulation on food intake and body mass," *J Physiol Pharmacol* 2004; 55:155-163, examined the effects of neuromodulation of the vagus using an implanted microchip. The study noted that such electrical stimulation reduced fasting glucose levels and that this effect was enhanced when combined with capsaicin treatment, which supports a role for the vagus in glucose homeostasis.

Another study Forster et al., "Gastric pacing is a new surgical treatment for gastroparesis," *Am J Surg* 2001; 182(6): 676-681, stimulated the antral part of the stomach with a low energy signal and achieved a decrease in the severity and frequency of nausea and vomiting. This result demonstrates that afferent vagal information could be modulated not only by vagal stimulation but also by gastric stimulation.

Stimulation may occur, and be effective, at one or more sites. For example, direct stimulation of the antral part of the stomach may be used to introduce antiperistaltic gastric waves to decrease food intake or stimulation of ventral vagus may be used to reduce food intake. As already mentioned, different stimulation parameters and nerve size (e.g., diameter) can play a role in the end result caused by electrical stimulation. Stimulation of the stomach to cause contraction of the stomach is discussed in detail further below with reference to FIG. 7.

As already mentioned, vagal afferents 460 conduct signals from the stomach 420 to the NTS 484 carrying information about the size and chemical composition of a meal, which is transmitted by other specific connections to satiety connections in the brain 480. Studies of food intake support that electrical stimulation of the anterior vagal nerve 460 can increase afferent traffic, which, in turn, influences function of satiety connections. At the central level, such electrical stimulation can decrease food intake and body weight.

Sensing Vagal Activity

While direct or indirect electrical nerve stimulation can achieve various effects (e.g., increase activity, selective activity, blocking of unidirectional or bidirectional nerve traffic, etc.), nerve fibers or bundles can also be monitored for activity. As already discussed, vagal afferents are integral part of a negative feedback loop induced by constitution and size of food in GIT. A study by Krolczyk et al., "Encoding Meal in Afferent Vagal Discharge," *J. Physio. Pharma.* 2004; 55(1): 99-106, assessed vagal discharge in response to food and gastric distension in rats using a cuff electrode placed on the peripheral, afferent end of the right or left cervical vagus nerve at the level of the neck.

Data from the study showed that vagal input from the stomach code dynamic and static changes in response to gastric distension. In particular, the presence of food in duodenum elicited specific postprandial motility and activated vago-vagal reflexes to stimulate pancreatic secretion accompanied by a fall in plasma ghrelin and an increase of plasma leptin. The study noted that the chemical content of the food is most likely detected by duodenal nerve endings (chemoreceptors), whereas volume of a meal stimulates mechanoreceptors in upper gut, leading to distinct motility response.

The study of Krolczyk et al., noted other reports (using rat models) where a predominant nerve discharge comes from load sensitive mechanoreceptors of the stomach and that gastric volume more strongly signals for inhibition of food intake when compared to signaling by nutrient content.

In particular, the study of Krolczyk et al. showed that most intensive vagal response resulted from mechanical distension is induced by food intake; noting however, that there are significant differences in vagal activity related to chemical composition of given food. Thus, they concluded that not only size but also meal makeup influence food intake and that information related to size and makeup is at least partially encoded in vagal afferent discharge, beside the humoral signals.

More specifically, the study of Krolczyk et al., noted that the presence of chemically distinct food in the duodenum elicits clearly different afferent discharge in the vagus nerve and that two different patterns of vagal overall discharge are induced by food or gastric distension and those after meal are short lasting, which suggests a mechanism involving both signals from mechano- and chemoreceptors. The study concluded that food intake acts via neurohumoral routes of the brain-gut axis and that vagally mediated food induced negative satiety feedback loop acts via the following sequence of events: (i) size of meal in upper GIT (mechanoreceptors); (ii) chemical content in duodenum (chemoreceptors); and (iii) caloric load in liver (glucoreceptors).

With respect to actual signals sensed, the study noted that information collected form peripheral mechanoreceptors is encoded as combined amplitude-frequency and sequence spikes pattern in the vagus nerves only after short postprandial period. More specifically, left vagal afferents discharge rises with gastric distension of 6, 8 and 10 ml and were: 0.46+/−0.22 Hz, 0.65+/−0.31 Hz, 0.86+/−0.33 Hz respectively while similar discharge appeared in right vagal afferents: 0.41+/−0.08 Hz, 0.51+/−0.13 Hz and 0.77+/−0.27 Hz for 6, 8 and 10 ml of distension, respectively.

A, B and C Fibers

A nerve in the human body is typically composed of thousands of fibers, of different sizes, which may be designations by group (e.g., A, B and C). The vagus nerve, for example, may have approximately 100,000 fibers of various sizes (e.g., approximate diameters or cross-section) where each fiber can carry a signal. Normally, each axon (fiber) conducts in only one direction. Conduction velocity varies depending on size and other physiology such as myelination. The aforementioned A and B group fibers are myelinated, whereas C group fibers are unmyelinated.

Myelinated fibers are typically larger, conduct faster and have very low stimulation thresholds, compared to the unmyelinated type. Further, less energy is typically required to stimulate myelinated fibers, which exhibit a particular strength-duration curve that may relate to response for a given pulse width versus amplitude. In general, A and B group fibers can be stimulated with relatively narrow pulse widths (e.g., typically less than 1 ms). A group fibers conduct slightly faster than B group fibers and typically exhibit a slightly lower activation threshold. C group fibers are very small, conduct electrical signals very slowly, and have higher stimulation thresholds typically requiring a wider pulse width and higher amplitude for activation when compared to A and B group fibers. Hence, selective stimulation of only A and B group fibers may be achieved given appropriate equipment.

An exemplary method optionally includes control logic to classify sensed nerve activity where such classification may rely on groups such as A, B and C, myelinated/unmyelinated, etc. Activation of a nerve may rely on such classification. Activation may aim to transmit a signal or to block or inhibit a signal.

Sengupta et al. reported in *J. Neurophysiol.* 1989; 61(5): 1001-1010, that esophageal distension was associated with an afferent vagal discharge rate of approximately 30-50 Hz. Primarily C-fibers and A-delta fibers (the latter being classified by the investigators as esophageal tension afferents with conduction velocities of 2.5-22 m/s) were found to mediate these impulses. The data may indicate that vagal modulation at these frequencies and a duration of ten seconds will approximate a physiological response to gastric distension.

As described herein, inhibition or blocking of signals of a vagus nerve may be used for treating or controlling a metabolic disorder (e.g., consider the eating disorder anorexia nervosa). Activation of a vagal nerve is accompanied by generation of a signal or signals, assuming the nerve or nerve fibers is/are not in a refractory phase. Some stomach signals are carried by C-fibers, which become refractory if stimulated at high frequency (e.g., about 40 Hz or higher) for more than a period of 30 to 60 seconds. Thus, an exemplary method may aim to inhibit or block C-fiber transmission by through use of a scheme that delivers energy using a high frequency with a certain "on" time followed by an "off" time (e.g., consider about 300 seconds on followed by about 20 seconds). This scheme could be repeated for the interval of time that control (blocking of the C-fiber information) is desired to be exercised.

An alternative scheme may consider that C-fibers become refractory if stimulated for a sufficiently long period. Thus, an alternative scheme may continuously stimulate the C-fibers to render them refractory and thereby block nerve signal transmission. Again, various gut signals (e.g., stomach) are carried by C-fibers, hence, such blocking schemes may be appropriate on a continuous, a periodic or an as desired/needed basis (e.g., in response to an event, a signal, a schedule, etc.). C-fibers conduct more slowly than A and B-fibers; an exemplary scheme may account for such conduction differences, particularly when blocking certain C-fiber signals.

Energy Mechanisms—Thermogenesis

While various chemical and mechanical mechanisms have been discussed, other mechanisms such as so-called energy mechanisms exist. Evidence suggests that core temperature is involved in the termination of feeding. For example, an animal may eat to keep warm and stop eating to prevent hyperthermia. Trends show that eating commences shortly after temperature starts to rise and that eating terminates in association with a temperature peak. For example, evidence shows that a liver temperature of about 39.3° C. is associated with end of a meal.

Evidence exists that a mechanism in the liver is able to signal an elevation in core temperature, thereby suggesting a neural inhibition of feeding when temperature increases. Further reduced thermogenesis due to a lower liver temperature causes a delay in the termination of feeding (noting that diabetic subjects show a reduced thermogenic response to a glucose or insulin infusion compared to their controls—The question rises if modified vagal signaling also affects glucose homeostatic mechanisms). A study by Di Bella et al., "Behavioral patterns proceeding from liver thermoreceptors," Physiol Behav 1981; 26:53-59, found that feeding was inhibited after application of external heat to the liver.

Subdiaphragmatic denervation of the liver 460 abolishes this inhibition in food intake indicating the involvement of the hepatic vagal afferent 465 in this mechanism. Thus, all these studies demonstrate that there is a strong relation between (liver) temperature and meal termination and suggest that vagal afferents are important in thermosensitivity.

With respect to specific vagal pathways, a study by Zhang et al., "Thermosensitive transient receptor potential channels in vagal afferent neurons of the mouse", Am J Physiol Gastrointest Liver Physiol 2004; 286:G983-G991, demonstrates that afferent fibers in the hepatic branch of the vagus 465 are thermosensitive. More specifically, three types of thermosensitive unmyelinated fibers can be distinguished by cold (10° C. to 36° C.), warm (39° C. to 50° C.), and mixed (10° C. to 35° C. and 40° C. to 50° C.) temperatures, which suggests that the vagus nerve may mediate thermosensitivity.

Although in most experiments, the relation between satiety and thermogenesis is not directly studied, it could be that reduced thermogenesis in obese subjects causes a delay in satiety. One study found that in vagotomized rats the rise in thermic response following gastric intubation with a carbohydrate meal was diminished. Thus, it could be that a reduced afferent signaling could contribute to a decreased thermogenesis and thereby promoting obesity.

As described herein, various exemplary techniques optionally deliver energy to heat a vagal pathway and/or sense temperature. For example, in response to a decrease in liver temperature, one or more electrodes may be used to heat a vagal afferent or otherwise cause a response associated with an increased liver temperature.

Stimulation of Stomach

Various techniques exist for electrical stimulation of the stomach. Trials were performed using a canine model according to an exemplary arrangement 700 of FIG. 7 that included a proximal pair of electrodes 724 and a distal pair of electrodes 726 circumferentially positioned with respect to the stomach 420. Such an arrangement allows for delivery of energy to the stomach in a manner that accounts for transit time, direction, etc. For example, a timing sequence may call for delivery of energy to the proximal pair 724 and the distal pair 726 in a coordinated manner that facilitates emptying of the stomach 420. As described herein, energy delivered to the stomach may or may not cause contraction of stomach muscle. Energy insufficient to cause contraction of stomach muscle (e.g., due to delivery time, amplitude, frequency, etc.) may still, depending on conditions, lead to weight loss.

For various trials, the distal pair of electrodes 726 was configured in a bipolar manner for deliver energy to the stomach 420. A device 728 that included a timing mechanism and a power source was used to control delivery energy to the stomach 420 via the distal electrodes 726. Various trials used a pulse train with biphasic pulses delivered at a frequency of about 50 Hz, a duty cycle of about 100% and a per phase width of about 10 ms for a pulse width of about 20 ms. Various pulse train durations were used, generally in a range from about 4 seconds to about 6 seconds.

As C-fibers tend to respond more readily to stimulation with longer pulse width, pulse width was limited for delivery energy to the stomach. However, where C-fiber activation is desired, pulse width may be adjusted accordingly. As described herein, where an exemplary method aims to activate stomach muscle, a delivery scheme can use energy delivery parameters that aim to minimize effect on C-fibers. Such a scheme may, for example, minimize pain associated with C-fibers, accommodation or adaptation of C-fibers, etc.

As described herein, various exemplary techniques include delivery of energy to the stomach using a pulse width less than 20 ms. For example, a pulse train may use biphasic pulses with a phase width of about 1 ms (pulse width about 2 ms) and a delivery frequency of about 500 Hz to achieve a duty cycle of about 100%. In such an example, the shorter pulse width (and phase width) reduces activation of C-fibers while the high duty cycle ensures activation of stomach muscle or a beneficial affect on the stomach for purposes of controlling metabolism and/or feeding.

Table 1, below, provides examples of delivery schemes (S1 through S7) with reference to vagal activation and stomach muscle activation for various times (Time 1 through Time 4). The scheme S1 delivers energy in a manner that aims to primarily activate stomach muscle while the scheme S2 delivers energy in a manner that aims to primarily activate vagal nerves. In contrast, schemes S3-S7 deliver energy in a manner that aims to activate both stomach muscle and vagal nerves.

TABLE 1

Delivery Schemes

|    | Time 1 | Time 2 | Time 3 | Time 4 |
|----|--------|--------|--------|--------|
| S1 | S      | S      | S      | S      |
| S2 | V      | V      | V      | V      |
| S3 | S      | V      | S      | V      |
| S4 | S + V  | S      | S + V  | S      |
| S5 | S + V  | V      | S + V  | V      |
| S6 | S + V  | S + V  | S + V  | S + V  |
| S7 | S + V  | S      | V      | S + V  |

As noted in schemes S4-S7, energy may be delivered in a manner that aims to activate both stomach muscle and vagal nerves at a particular time (e.g., using different electrodes, at least one common electrode, the same electrodes). Overall, if a method aims to affect, at some point in time, the stomach muscles only, then a delivery scheme may be selected that minimizes its effect on C-fibers. Such a method may aim to reduce activation of C-fibers by reducing charge density delivered per pulse. In particular, the pulse width of the energy may be limited to a short duration (e.g., about 1 ms). Further, a delivery scheme that reduces charge density can reduce tissue damage. Yet further, in the scheme S3, where a particular region or site is used for both stomach and vagal activation, vagal nerves may be more responsive to delivered energy for Time 2 and Time 4 because they are not activated during Time 1 and Time 3. Thus, selective activation can enhance control or effectiveness of various schemes that aims to activate stomach muscle and vagal nerves.

In various trials, energy was delivered to a pair of distal electrodes 726 using a constant current, biphasic delivery scheme. Constant current refers to the current value during a particular phase of a pulse or, for example, to the peak-to-peak current for a biphasic pulse. Trials used different currents, typically in a range of about 2 mA to about 40 mA peak-to-peak. The delivery scheme used for the trials aimed to distribute energy by reducing the charge density delivered per pulse, which, again, included use of a limited pulse width.

Various trials used the arrangement 700 and delivery schemes with pulse widths less than 10 ms. An exemplary scheme used a biphasic pulse with a per phase width of about 1 ms delivered at a frequency of about 400 Hz. This scheme resulted in a desired effect on the stomach. With respect to contraction of stomach muscle, duty cycles were calculated using the following equation:

Duty Cycle (%)=Pulse Width per Phase (s)*No. of Phases*Frequency (Hz).

Thus, for pulse train with a biphasic pulse and a pulse width of 1 ms, delivered at 400 Hz, the duty cycle was 80%. With respect to train duration, a train may be delivered for about 1 s to about 20 s.

Various exemplary methods may include delivery schemes according to one or more parameter settings or values selected from the ranges below:
Energy Injection Mode: Constant Voltage or Constant Current
  Pulse Amplitude: ~0 V to 16V peak-to-peak
  ~0 mA to 40 mA peak-to-peak
  Pulse Width (per phase): ~10 μs to 10 ms
  Frequency (of train): ~0 Hz to 500 Hz
  Pulse Morphology Biphasic (active or capacitive)
  Duty Cycle: ~0% to 100%

Figure 7:
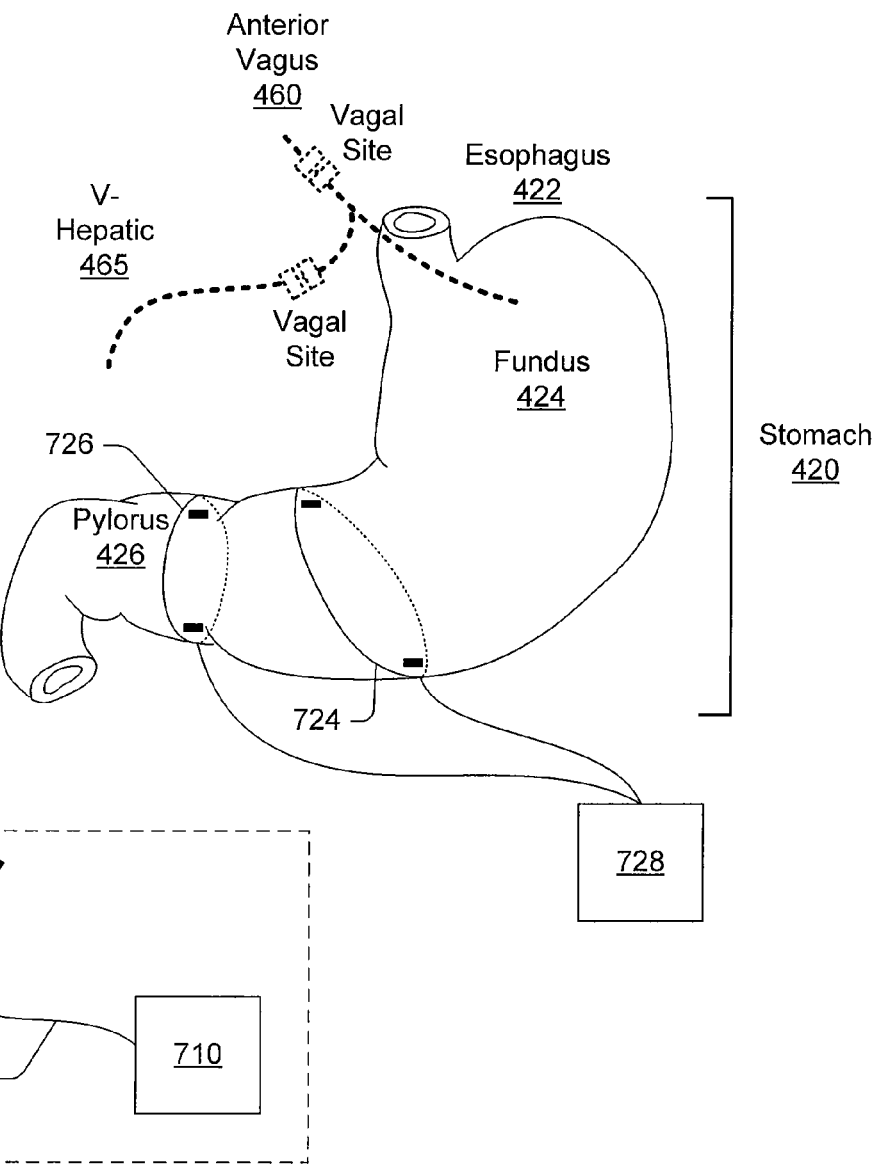
FIG. 7 is a diagram of an exemplary stimulation arrangement that includes two implantable devices where one of the devices provides for stimulation of the stomach and optionally sensing activity of the stomach.

The exemplary arrangement 700 of FIG. 7 optionally includes an implantable device 710 that includes one or more electrode bearing leads 712. According to the exemplary arrangement 700, the device 710 and the device 728 may communicate uni- or bi-directionally. The device 710 may include features of the devices 110, 112, 114, 118 of FIG. 1 and/or the device 200 of FIG. 2. For example, the device 710 may include features for stimulation of a vagal nerve and optionally perform such stimulation in a manner coordinated with stomach stimulation.

FIG. 7 also shows two possible vagal activation locations. One location is on the anterior vagus 460 prior to the hepatic branch 465 and/or the pyloric branch 468 (see FIG. 4). While the dashed lines indicate electrode pairs, one or more electrodes may be located at either location. The electrodes may be associated with a stomach activation device (e.g., the device 728), a dedicated vagal activation device (e.g., the device 710), or any appropriate device capable of delivering activation energy to the vagal nerve.

An exemplary method for delivering energy for vagal nerve activation includes use of a delivery scheme where one or more parameter values are selected from the ranges below:
  Pulse Amplitude: ~0 mA to 10 mA per phase
  Pulse Width (per phase): ~100 μs to 1 ms
  Frequency (of train): ~0 Hz to 100 Hz
  Pulse Morphology Biphasic (active or capacitive)
  Duty Cycle: ~0% to 100%

Various exemplary methods disclosed herein optionally include delivery of energy to smooth muscle of at least a portion of the GIT where the portion of the GIT defines a longitudinal axis extending therethrough. Such delivery of energy may include delivery at a proximal location to the smooth muscle circumferentially about the portion of the GIT in a plane (e.g., substantially perpendicular) intersecting the longitudinal axis where the energy is sufficient to activate the smooth muscle to produce a local circumferential contraction at the proximal location. Such exemplary methods may optionally include delivery of energy to at least one distal location to the smooth muscle circumferentially about the portion of the GIT in a plane (e.g., substantially perpendicular) intersecting the longitudinal axis where the energy is sufficient to activate the smooth muscle to produce a local circumferential contraction at the distal location. Further, such optional delivery of energy may include phase-locking such that the energy is delivered at the proximal and distal locations successively and repetitively.

Sensing Activity of the GIT

While various methods, devices, systems, etc., may include sensing of vagal activity, sensing of other GIT activity may be used. Such sensing may be achieved via implantable sensors and/or via external sensors.

In some early studies of gastric electrical activity, the term "electrogastrography" (EGG) was used for any extracellular recordings performed in vivo. This term is, however, now used almost exclusively for cutaneous recordings of gastric electrical activity obtained with abdominal electrodes. For example, a study by Chen et al., "Response of the electric activity in the human stomach to water and a solid meal," *Med Biol Eng Comput*. 1991 July; 29(4):351-357, used EGG surface electrodes to measure gastric electrical activity. The measured activity was analyzed using power spectral analysis and statistical analysis techniques.

Standard electrocardiographic (EKG) electrodes arranged in different configurations on the abdomen are routinely used for bipolar EGG recordings. Thus, a programmer for an implantable cardiac therapy that includes EKG features may be suitable for use in acquiring EGG information, including pre-prandial information, and communicating such information or results of an analysis thereof to an implantable device for food intake therapy.

As already mentioned, an exemplary method includes acquiring pre-prandial information using one or more techniques such as EGG prior to deciding whether to implant a device for delivery of food intake therapy or to implement therapy that relies on acquisition of pre-prandial information.

FIGS. 8A and 8B show an exemplary system 800 and an associated exemplary method 840. A EGG device 804 having one or more leads 806 and electrodes 808, 808' is fitted to sense electrical activity of a patient 401. The exemplary method 840 includes commencing EGG acquisition 842 and then providing a food stimulus 844 to the patient 401. A decision block 848 decides if the EGG exhibits a physiological response to the food stimulus 844.

If the decision block 848 decides, based on an analysis of the EGG, that no response exists or no reliable response exists then the method enters a low probability of success block 852. The low probability block 852 indicates that the patient 401, in response to a food stimulus, may not generate electrical activity sufficient for use in a control algorithm. However, if the decision block 848 decides that the EGG exhibits a physiological response to the food stimulus 844, then the method enters a higher probability of success block 856 that prompts a care provider to consider implementation of an implantable device that relies, at least in part, on pre-prandial information. Probability of success may be determined according to a model, data from trials, etc. Accordingly, acquired response information may be compared to historical response information for patients treated successfully, patients unsuccessfully treated and/or patients tested but not treated.

While the system 800 and associated method 840 rely on an external sensing technique for pre-prandial information, in an alternative, a more invasive technique may be used such as a technique that involves implantation of one or more electrodes or sensors and optionally implantation of associated electronics (see, e.g., the device 200 of FIG. 2). In this alternative scenario, the method block 842 may be replaced with an appropriate action and, correspondingly, the decision block 848 relies on such action.

An exemplary method includes initiating acquisition of an electrogastrograph, during the acquisition of the electrogastrograph, applying a food stimulus, analyzing the electrogastrograph for indicia of a pre-prandial response to the food stimulus and, if the electrogastograph comprises indicia of a pre-prandial response to the food stimulus, then deciding to implant, in a patient, an implantable device configured to acquire information indicative of a pre-prandial response and to deliver an anti-obesity therapy based at least in part on acquired information.

Figure 9A:
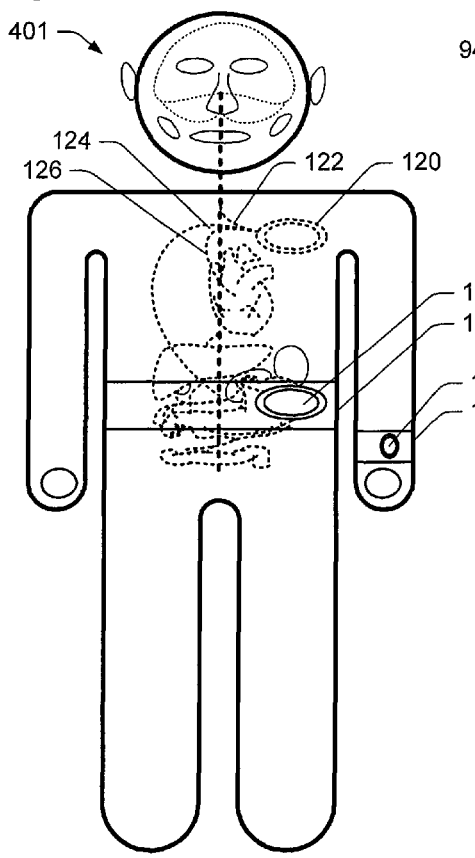
FIG. 9A is a diagram of an arrangement for helping to decide whether a patient should be subject to particular therapy and FIG. 9B illustrates an associated method for determining if the patient is in a pre-prandial phase and FIG. 9C illustrates exemplary plots of sensed information using a similar arrangement where the sensed information exhibits pre-prandial information.
Figure 9B:
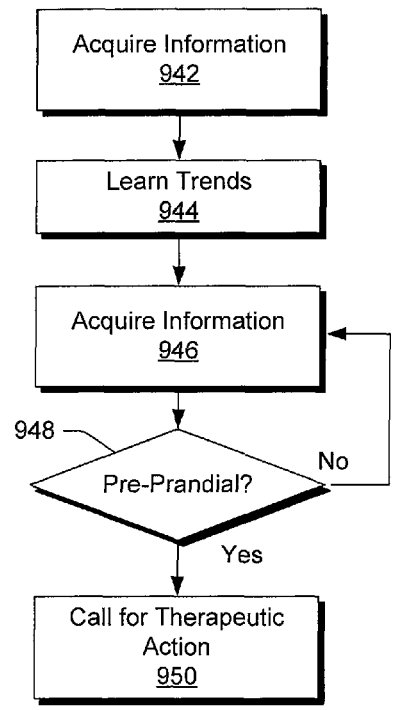
Figure 9C:
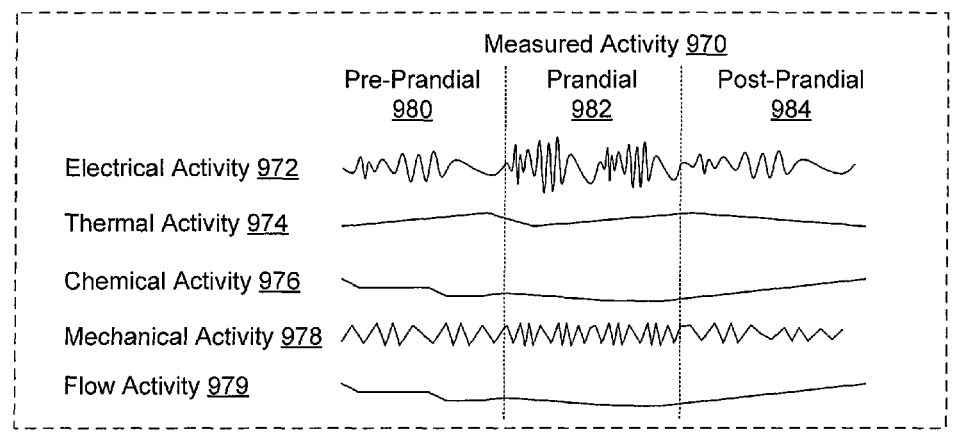

FIG. 9 shows an exemplary system 900 and associated method 940. According to the system 900, a patient 401 is fitted with one or more devices. For example, device 120 is an implantable device that includes one or more leads. As shown, the device 120 includes a nerve/muscle lead 122 that allows for sensing information and/or delivery of energy to nerves and/or muscles associated with the upper digestive system; a cardiac lead 124 that allows for sensing information and/or delivery of energy to nerves and/or the myocardium; and a nerve/muscle lead 126 that allows for sensing information and/or delivery of energy to nerves and/or muscles associated with the lower digestive system (e.g., nerves, organs, etc., of the abdomen). The device 120 may delivery cardiac therapy and therapy related to food intake.

The device 140 is an external device positioned on the patient 401 through use of a band 145. The device 140 may sense information and communicate such information to an implantable device such as the device 120. For example, the device 140 may include a series of electrodes mounted on the band 145 configured to acquire signals associated with digestion (e.g., EGG, etc.). The device 140' may be used as an alternative to the device 140 or in conjunction with the device 140. The device 140' mounts to a wrist of the patient 401 through use of a band 145' to sense information and optionally communicate such information to an implantable device and/or an external device. The device 140' optionally provides for delivery of energy to the patient 401. For example, the device 140' may delivery energy to signal the patient 401, to activate an acupuncture point, etc. The device 140 or 140' may include any of a variety of mechanisms for alerting the patient 401. For example, a light, a buzzer, etc., may indicate that feeding should be avoided or that feeding should proceed. An external device such as the device 140 may acquire finger pulse amplitude information while an implantable device such as the device 120 may receive the information or an instruction from the device 140 and, in response, deliver an appropriate therapy.

An exemplary method 940 includes an acquisition block 942 for acquiring information from a patient. A learning block 944 uses the acquired information to learn trends, in particular, trends associated with patient feeding. After learning, more information is acquired per the acquisition block 946. A decision block 948 decides, based on the acquired information of block 946, if the patient is in a pre-prandial phase. If the decision block 948 decides that the patient is not in a pre-prandial phase, then the method 940 continues in the acquisition block 946. However, if the decision block 948 decides that the patient is in a pre-prandial phase, then the method 940 continues in a call block 950 that calls for therapeutic action. Such action may act to suppress the patient's appetite, confirm that feeding should proceed, etc., as appropriate. For example, the block 950 may call for delivery of energy to the anterior or posterior vagus to induce satiety and/or call for delivery of energy to the stomach to induce satiety.

FIGS. 9A and 9B also show a plot 970 of measured activity during a pre-prandial phase 980, during a prandial phase 982 and during a post-prandial phase 984 (e.g., following eating). Measured activities include electrical activity 972, thermal activity 974, chemical activity 976, mechanical activity 978 and flow activity 979. A device (e.g., device 120, 140, 140') may measure one or more of the activities 972, 974, 976, 978 to aid in delivery of one or more therapeutic therapies.

Pre-prandial electrical activity 972 may include an increase in vagus nerve activity, an increase in gastric electrical activity, an increase in heart rate (e.g., IEGM, ECG) and/or a change in skin conductance. Pre-prandial thermal activity 974 may include an increase in thermal activity of the stomach muscle and/or a change in liver temperature. Pre-prandial chemical activity 976 may include a drop in pH of the contents of the stomach (e.g., luminal temperature) and/or a change in oxygen concentration (e.g., blood spectrophotometry).

Pre-prandial mechanical activity 978 may include changes in pressure, movement of a muscle, etc. A sensor for sensing mechanical activity may rely on a force transducer, a pressure transducer, a strain transducer, an accelerometer, etc. For example, an implantable lead may include a sensor embedded in muscle (e.g., stomach, muscles activated during swallowing, etc.). With respect to swallowing, a patient may begin swallowing in response to increased salivation associated with a pre-prandial phase.

Pre-prandial flow activity 979 can include activity such as blood flow, saliva flow, gastric substance flow, etc. For example, an increase in blood flow through the hepatic portal vein 452 (see FIG. 5) may occur during one or more phases. Such flow may be associated with liver metabolism and a change in liver temperature.

An exemplary method may delivery tiered therapy where a change in tier corresponds to a change in phase (e.g., pre-prandial, prandial, post-prandial). For example, a first tier may deliver electrical energy to the vagus while a second tier may delivery electrical energy to the stomach muscle. In this example, the first tier may correspond to a pre-prandial phase while the second tier may correspond to a prandial phase. The second tier optionally includes delivery of electrical energy to the vagus in combination with delivery of electrical energy to the stomach muscle. Upon entering a post-prandial phase, the second tier therapy may be discontinued while the first tier therapy is continued for a pre-determined amount of time (e.g., according to a timer or a schedule). In general, such a method delivers more energy per pulse to the stomach muscle than to the vagus. Thus to economize longevity of an implantable device with a limited power supply, an exemplary method may use a tiered therapy that delivers energy to the stomach less frequently than to the vagus.

An exemplary method delivers energy to the vagus on a substantially continuous basis and delivers energy to the stomach on an as needed basis, for example, upon entry of a pre-prandial phase or a prandial phase. For example, a sensor may sense information that indicates that a patient has entered a pre-prandial phase. In response, a device can call for delivery of energy to the stomach to induce satiety. With respect to detection of a prandial phase, a sensor that can detect stretching of the fundus (e.g., an increase in volume of fundus) may be used to indicate food intake.

An exemplary method includes a learning algorithm that screens acquired information for evidence of pre-prandial activity. For example, an exemplary implantable device acquires information while a patient records feeding times. The acquired information and the feeding record are then input to an external computing device that screens the acquired information for indicia that correlates with feeding times. After identification of such indicia, the implantable device is appropriately programmed to detect pre-prandial activity. For example, if a periodic signal increases frequency during a pre-prandial phase, then the implantable device may be programmed to detect an increase in frequency as indicative of a pre-prandial phase. An exemplary method optionally acquires information from a pacemaker (e.g., IEGMs) implanted in a patient and analyzes the IEGMs with respect to feeding times for the patient. In turn, the implanted device is programmed to analyze IEGMs for indicia of the patient being in a pre-prandial phase.

An exemplary method for treating obesity, implemented at least in part by a computing device, includes calling for delivery of electrical energy to a vagal nerve, detecting pre-prandial activity and, in response to the detection of pre-prandial activity, calling for delivery of electrical energy to the stomach for a pre-determined amount of time to induce satiety. In such a method, subsequent delivery of electrical energy to a vagal nerve may deliver electrical energy to a branch of the anterior vagal nerve. One or more parameters of energy delivery may be adjusted to avoid unwanted gag response or vomiting. With respect to delivery of energy to a vagal nerve, in response to the detection of pre-prandial activity, such delivery may be ceased for a pre-determined amount of time. Alternatively, such delivery may continue while energy is delivered to the stomach. Further, an exemplary method may include delivering energy continuously, or periodically, to a vagal nerve, for example, at a pre-determined pulse frequency.

With respect to duration of delivering energy to the stomach, the pre-determined amount of time may be less than about 1 hour, less than about 30 minutes or limited by another appropriate time as desired (e.g., based on patient trials, etc.).

As already mentioned, a method may include detecting pre-prandial activity by analyzing a sensed signal such as an electrical activity signal of a vagal nerve, and/or an electrical activity signal of the stomach muscle. Detection may rely on a signal frequency, for example, a sensed signal may include or reach a frequency indicative of pre-prandial activity.

Figure 10:
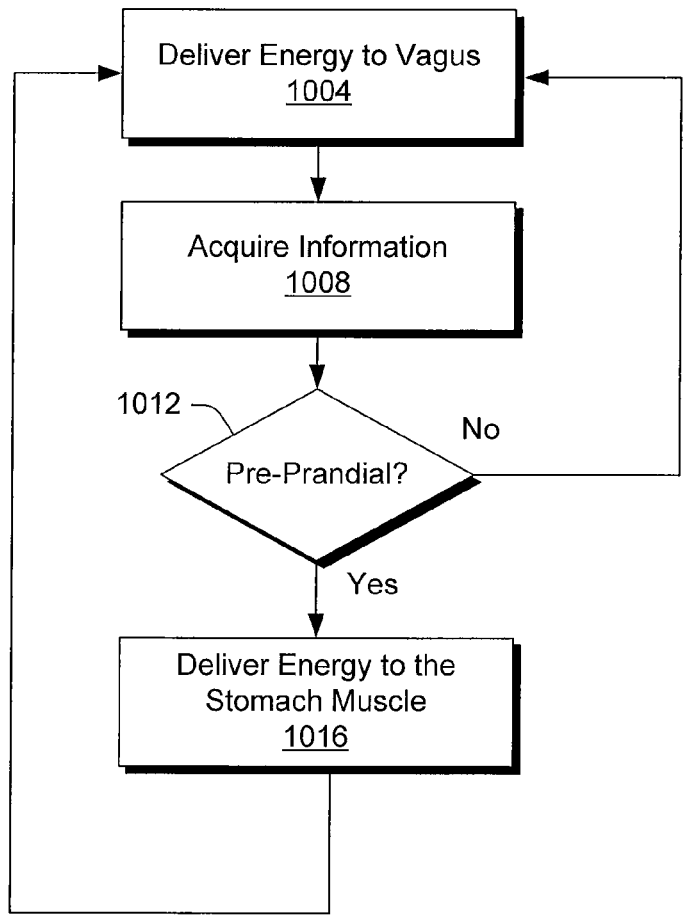
FIG. 10 is a block diagram of an exemplary method for delivering a therapy to induce satiety.

FIG. 10 shows an exemplary method 1000 for inducing satiety. The method 1000 commences in a delivery block 1004 that delivers energy to the vagus. An acquisition block 1008 acquires information, for example, via one or more sensors (implanted or external) to sense activity such as electrical activity, temperature activity, chemical activity, mechanical activity, flow activity, etc. A decision block 1012 decides if a patient is in a pre-prandial phase based at least in part on the acquired information. If the decision block 1012 decides that the patient is not in a pre-prandial phase, the method 1000 continues delivery of energy to the vagus (e.g., per the delivery block 1004). However, if the decision block 1012 decides that the patient is in a pre-prandial phase, then the method 1000 enters a delivery block 1016 to deliver energy to the stomach muscle to induce satiety. The delivery block 1016 may operate according to a timer, for example, to delivery energy to the stomach muscle for a period of about 20 minutes. In a particular example, the acquisition block 1008 acquires efferent vagal activity as an indicator of pre-prandial phase.

An exemplary method, such as the method 1000, may take one or more actions based on frequency of pre-prandial events. For example, many physiologic signals are periodic. Where an acquisition block acquires information for a periodic signal, frequency of the signal may be used to adjust a therapeutic action (e.g., adjust one or more parameters for delivery of energy to the vagus and/or to the stomach muscle). An exemplary method may acquire information and use the information in a feedback loop to adjust delivery of energy to the vagus or to the stomach muscle. For example, an adjustment may adjust energy, duty cycle, frequency, etc., of energy delivered to the vagus and/or to the stomach muscle.

An exemplary method, performed at least in part by an implantable computing device, includes acquiring information (e.g., electrical activity, thermal activity, chemical activity, mechanical activity and flow activity), comparing the acquired information to one or more criteria to detect a pre-prandial response and, upon detection of a pre-prandial response, calling for one or more therapeutic actions to induce satiety. In such an example, the acquired information may be electrical activity of the vagus (e.g., efferent activity), electrical activity of the stomach, mechanical activity of the stomach, skin conductivity (e.g., using at least one cutaneous electrode), etc. Such a method may include providing a food stimulus, acquiring information during the food stimulus and analyzing the acquired information to determine the one or more criteria to detect a pre-prandial response.

Figure 11:
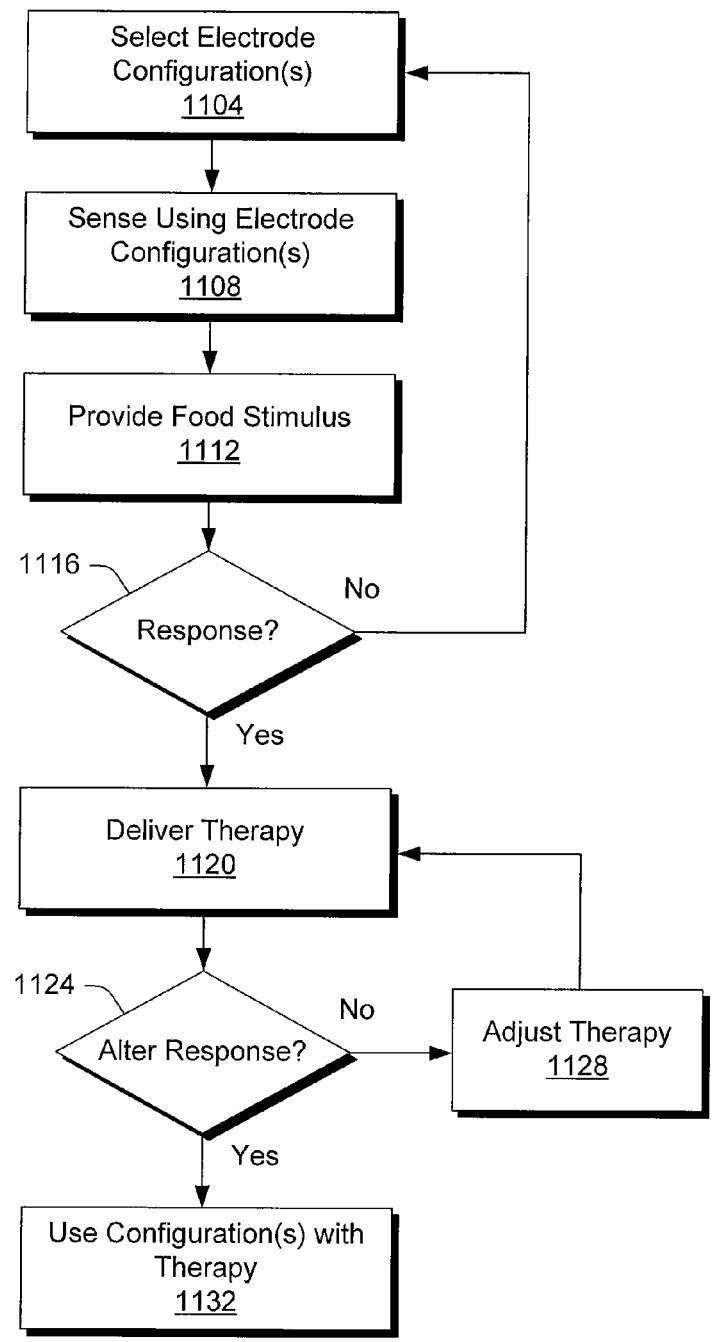
FIG. 11 is a block diagram of an exemplary method for selecting one or more electrode configurations and deciding whether to use a selected configuration with a deliverable therapy.

FIG. 11 shows an exemplary method 1100 for selecting one or more electrode configurations for use with a therapy related to food intake. The method 1100 may be implemented using an arrangement such as the arrangement 700 of FIG. 7 or a system such as the system 800 of FIG. 8 or the system 900 of FIG. 9. The method 1100 commences in a selection block 1104 that selects one or more electrode configurations for sensing pre-prandial activity. A sense block 1108 senses for pre-prandial activity using the selected electrode configuration(s). Next, in a provision block 1112, a subject is provided with a food stimulus or stimuli. A decision block 1116 follows that decides if information acquired via sensing exhibits pre-prandial activity (e.g., a pre-prandial response).

In the case that the decision block 1116 decides that the information does not exhibit pre-prandial activity, then the method 1100 continues at the selection block 1104 to select one or more other electrode configurations that may be able to sense pre-prandial activity. In the case that the decision block 1116 decides that the information exhibits a response, then the method 1100 continues in a delivery block 1120 that delivers an appropriate therapy.

With respect to the delivered therapy, the method 1100 may deliver a therapy aimed at squelching or enhancing the pre-prandial activity. For example, an implantable device (see, e.g., the devices 110, 112, 114, 118, 120) may delivery stimulation energy via one or more electrodes to block efferent vagal activity such as vagal activity associated with a cephalic phase response. Such therapy may rely on other information as well, for example, a feeding schedule.

After delivery of therapy 1120, the method 1100 enters another decision block 1124 that decides whether the delivered therapy altered the response. For example, sensing may occur during delivery of therapy or be halted during delivery of therapy and re-commenced after delivery of therapy. Information acquired during or after delivery of therapy may be compared with other information to help decide if the therapy altered the response in a desirable manner.

In the case that the decision block 1124 decides that the therapy did not alter the response, then the method 1100 continues in an adjustment block 1128 that adjusts the therapy and continues to delivery the adjust therapy per the delivery block 1120.

In the case that the decision block 1124 decides that the therapy did adequately alter the response, then the method 1100 continues in a use block 1132 that indicates that use of the selected configuration(s) and therapy are appropriate.

As described herein, various exemplary devices, methods, systems, etc., optionally rely on a system such as the system 900 to acquire pre-prandial information and then rely, at least in part, on such information in a subsequent action. For example, such information may be used to indicate that a patient intends to eat and that, if the eating is unscheduled or otherwise unwarranted, then a particular therapy may be implemented by an implantable device to thereby alter food intake (e.g., prevent or reduce intake of food by the patient).

Various techniques for acquiring pre-prandial information may be used including techniques that measure reaction to food exposure (e.g., food stimuli) such as measuring changes in heart rate, heart rate variability (HRV), salivation, blood pressure, skin conductance and gastric activity.

With respect to action based on information of pre-prandial activity, such action can include stomach muscle stimulation, afferent nerve stimulation, efferent nerve stimulation, etc. For example, given that an increase in mechanical and/or electrical activity of the antrum of the stomach without actual intake of food, the driving mechanism is likely to include efferent signals carried by the vagus. In particular, the posterior vagus is known to act as an efferent pathway to the GIT. Thus, upon detection of pre-prandial mechanical and/or electrical activity, an implantable device may respond by blocking a portion of the posterior vagus.

As already mentioned, techniques exist for sensing vagal activity. An exemplary method optionally includes sensing efferent vagal activity, deciding that such activity is pre-prandial and then calling for one or more appropriate actions, if warranted.

A study by Rogers et al., "Cephalic phase of colonic pressure response to food," *Gut*. 1993 April; 34(4):537-43, examined cephalic stimuli such as food discussion, sight and smell of food without taste, smell of food without sight or taste, and sight of food without smell or taste. This study reported that food discussion significantly increased colonic pressure activity compared with control or basal activity; that smell of food without sight or taste significantly increased the colonic pressure activity compared with control and basal periods; that sight and smell of food without taste significantly increased colonic pressures compared with control but not basal activity; and that the increase in colonic activity after sight of food without smell or taste was not significantly different from control or basal activity while food discussion was the strongest colonic stimulus tested. Further, increased colonic pressure activity after food discussion correlated significantly with gastric acid output. As described herein, an exemplary device, method, system, etc., optionally acquires information as to colonic pressure and analyzes the information as to intent to feed.

In some instances, a patient may benefit from initiation of a cephalic phase or boosting of cephalic phase activity or cephalic phase duration. For example, a study by Pedersen, "Sonographic comparison of gastric emptying of broth and water: is there a promoting cephalic factor?" *Acta Radiol.* 2005 April; 46(2):132-134, examined the emptying times of broth and water to explore the possibility of a cephalic influence on gastric emptying. The study concluded that broth empties faster from the stomach than plain water, probably because of a "cephalic phase" stimulation of gastric motility via the vagus nerve.

A study by Sobhani et al., "Vagal stimulation rapidly increases leptin secretion in human stomach," *Gastroenterology.* 2002 February; 122(2):259-263, analyzed the effect of insulin-induced vagal stimulation on leptin release in the human stomach and reported that insulin caused a rapid increase in leptin output in men without vagotomy but not in those with vagotomy. The study concluded that vagal stimulation of leptin release in the human stomach suggests that leptin is released during the cephalic phase of gastric secretion and that luminal leptin may be involved in vagus-mediated intestinal functions.

An exemplary method optionally initiates, enhances and/or extends a cephalic phase for a patient in response to a schedule, sensed activity or other information. Such action may occur via stimulation of a vagal efferent to the GIT. For example, for a person without an impaired response to food stimuli yet without impairment in efferent vagal pathway to the GIT may benefit from such stimulation.

Figure 12:
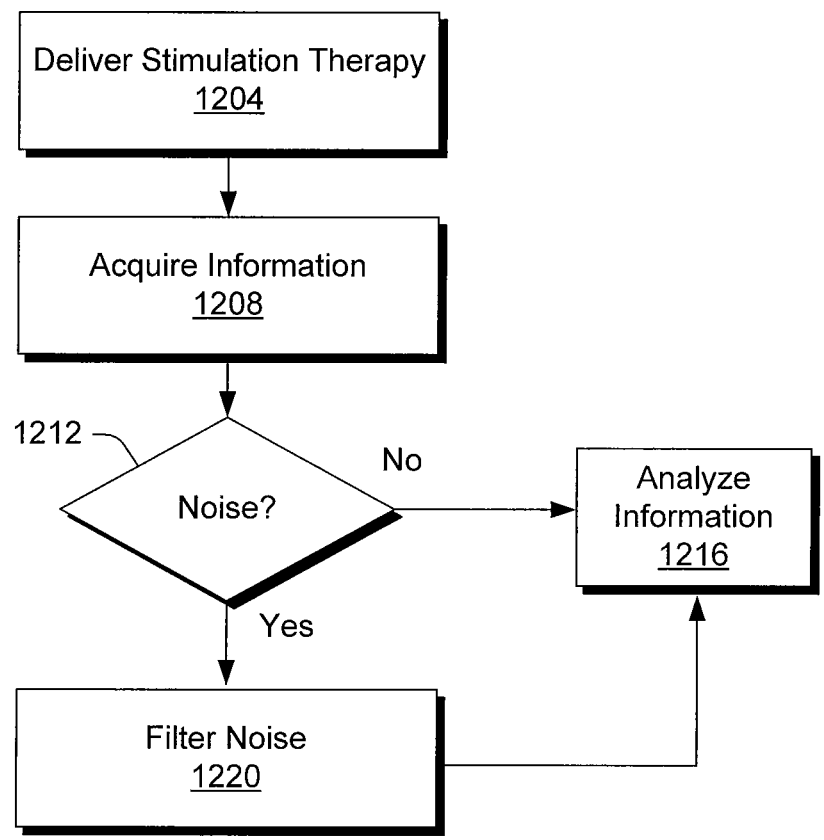
FIG. 12 is a block diagram of an exemplary method for deciding whether noise exists due to a stimulation therapy and to filter such noise.

FIG. 12 shows an exemplary method 1200 for analyzing sensed information. The exemplary method 1200 is suitable for use where a stimulation therapy is being delivered or may be delivered. For example, cardiac pacing therapy relies on delivery of stimulation energy to pace the heart. Depending on a variety of factors (e.g., energy, electrode configuration, etc.), the pacing stimuli may interfere with sensing of activity associated with food intake.

The exemplary method 1204 includes a stimulation therapy block 1204 where a patient undergoes one or more types of stimulation therapy (e.g., obesity, respiratory, cardiac, etc.). An acquisition block 1208 follows that includes sensing information, for example, that can indicate whether a patient is in or entering a cephalic phase. A decision block 1212 decides if noise is present due to delivery of one or more stimulation therapies. If noise is not present, then the method 1200 enters an analysis block 1216 to analyze the acquired information. However, if the decision block 1212 decides that noise is present, then the method 1210 enters a filter block 1220 that filters the noise and continues to the analysis block 1216.

In an alternative, where noise is detected, gating may occur or delay in acquisition in an attempt to avoid the noise. With respect to gating, such gating may be adaptive and based at least in part on the detected noise. In instances where an implantable device for delivery of stimulation therapy communicates with an implantable device for sensing, then coordination between the sensing and stimulation therapy may occur to avoid noise in the sensing.

Conclusion

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:

1. An implantable device comprising:
    means for sensing one or more physiologic signals associated with pre-prandial activity,
    means for delivering electrical energy to a vagal nerve prior to detection of pre-prandial activity;
    means for detecting pre-prandial activity from the sensed one or more physiologic signals; and
    in response to the detection of pre-prandial activity, means for delivering electrical energy to the stomach for a predetermined period of time to induce satiety.

2. The device of claim 1 wherein the means for delivering electrical energy to a vagal nerve comprises means for delivering electrical energy to a branch of the anterior vagal nerve.

3. The device of claim 1 wherein the means for delivering electrical energy to a vagal nerve delivers electrical energy at level insufficient to induce vomiting.

4. The device of claim 1 wherein the means for delivering electrical energy to a vagal nerve comprises means for continuously delivering energy at a pre-determined frequency.

5. The device of claim 1 wherein the means for detecting pre-prandial activity comprise means for sensing electrical activity of a vagal nerve.

6. The device of claim 1 wherein the means for detecting pre-prandial activity comprise means for sensing electrical activity of the stomach.

7. The device of claim 1 wherein the means for detecting pre-prandial activity comprise means for sensing an electrical signal having a frequency indicative of pre-prandial activity.

8. The device of claim 1 wherein the means for the delivery of electrical energy to the vagal nerve comprises means for the delivery of electrical energy to the vagal nerve prior to the detection of pre-prandial activity and further comprising, means for terminating the delivery of electrical energy to the vagal nerve in response to the detection of pre-prandial activity.

9. An implantable device comprising:
    a processor configured to control operation of the implantable device;
    a vagal pulse generator coupled to the processor, the vagal pulse generator being configured to deliver electrical energy to a vagal nerve under the control of the processor prior to detection of pre-prandial activity;
    one or more sensors coupled to the processor, the one or more sensors being configured to detect one or more parameters indicative of a pre-prandial response wherein the processor is configured to process the one or more parameters to detect a pre-prandial response; and
    a stomach pulse generator coupled to the processor, the stomach pulse generator being further coupled to a portion of the stomach and configured to deliver electrical energy to the stomach for a pre-determined amount of time in response to the detection of a pre-prandial response by the processor.

10. The device of claim 9 wherein the one or more sensors are configured to detect at least one type of activity selected from a group consisting of electrical activity, thermal activity, chemical activity, mechanical activity and flow activity; the processor being configured to compare the one or more parameters to one or more criteria to detect a pre-prandial response; and, upon detection of a pre-prandial response, to call for one or more therapeutic actions to induce satiety.

11. The implantable device of claim 9 wherein the one or more sensors measure at least one type of activity selected from a group consisting of electrical activity, thermal activity, chemical activity, mechanical activity and flow activity.

* * * * *